United States Patent
Eggers et al.

(10) Patent No.: US 6,896,672 B1
(45) Date of Patent: *May 24, 2005

(54) METHODS FOR ELECTROSURGICAL INCISIONS ON EXTERNAL SKIN SURFACES

(75) Inventors: Andrew R. Eggers, Ostrander, OH (US); Philip E. Eggers, Dublin, OH (US); Ronald A. Underwood, Belmont, CA (US); Stephen M. Brunell, Mountain View, CA (US); Hira V. Thapliyal, Los Altos, CA (US)

(73) Assignee: Arthrocare Corporation, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/562,650

(22) Filed: May 1, 2000

Related U.S. Application Data

(60) Division of application No. 09/162,117, filed on Sep. 28, 1998, now Pat. No. 6,117,109, which is a continuation-in-part of application No. 08/977,845, filed on Nov. 25, 1997, now Pat. No. 6,210,402, which is a continuation-in-part of application No. 08/562,332, filed on Nov. 22, 1995, now Pat. No. 6,024,733.

(51) Int. Cl.[7] .......................... A61B 18/12; A61B 18/14
(52) U.S. Cl. ........................ 606/32; 606/41; 604/114; 607/99
(58) Field of Search ................ 606/32, 34, 41, 606/45, 48–50; 604/114; 607/99

(56) References Cited

U.S. PATENT DOCUMENTS

| | | |
|---|---|---|
| 2,056,377 A | 10/1939 | Wappler |
| 3,815,604 A | 6/1974 | O'Malley et al. |
| 3,828,780 A | 8/1974 | Morrison, Jr. et al. |

(Continued)

FOREIGN PATENT DOCUMENTS

| | | | |
|---|---|---|---|
| DE | 3930451 | 3/1991 | ........... A61B/17/39 |
| EP | 0 703 461 | 3/1996 | ........... G01R/27/02 |
| EP | 0 740 926 A2 | 11/1996 | ........... A61B/17/39 |

(Continued)

OTHER PUBLICATIONS

US 5,326,343, 7/1994, Rudie (withdrawn)
Pearce, John A. (1986) *Electrosurgery*, pp. 17, 69–75, 87, John Wiley & Sons, New York.
J.W. Ramsey et al., *Urological Research* vol. 13, pp. 99–102 (1985).
V.E. Elsasser et al. *Acta Medicotechnica* vol. 24, No. 4, pp. 129–134 (1976).
P.C. Nardella (1989) *SPIE* 1068:42–49 Radio Frequency Energy and Impedance Feedback.

(Continued)

*Primary Examiner*—Lee Cohen
(74) *Attorney, Agent, or Firm*—John T. Raffle; Richard R. Batt

(57) ABSTRACT

Systems and methods are provided for removing fatty tissue underlying a patient's epidermis (e.g., blepharoplasty, brow lifts, eyelid shortening procedures, and the like). These methods include positioning one or more active electrode(s) and one or more return electrode(s) in close proximity to a target site on an external body surface of the patient. A high frequency voltage difference is applied between the active and return electrode(s), and the active electrode(s) are translated across the external body surface to create an incision therein. The bipolar configuration controls the flow of current to within and around the distal end of the probe, which minimizes tissue necrosis and the conduction of current through unwanted paths in the patient. The residual heat from the electrical energy also provides simultaneous hemostasis of severed blood vessels, which increases visualization and improves recovery time for the patient.

12 Claims, 24 Drawing Sheets

U.S. PATENT DOCUMENTS

| | | | |
|---|---|---|---|
| 3,901,242 A | 8/1975 | Storz | |
| 3,920,021 A | 11/1975 | Hiltebrandt | |
| 3,939,839 A | 2/1976 | Curtiss | |
| 3,970,088 A | 7/1976 | Morrison | |
| 4,040,426 A | 8/1977 | Morrison, Jr. | |
| 4,043,342 A * | 8/1977 | Morrison, Jr. | 606/48 |
| 4,074,718 A | 2/1978 | Morrison, Jr. | |
| 4,092,986 A | 6/1978 | Schneiderman | |
| 4,116,198 A | 9/1978 | Roos | |
| 4,181,131 A | 1/1980 | Ogiu | |
| 4,184,492 A | 1/1980 | Meinke et al. | |
| 4,202,337 A | 5/1980 | Hren et al. | |
| 4,228,800 A | 10/1980 | Degler, Jr. et al. | |
| 4,232,676 A | 11/1980 | Herczog | |
| 4,248,231 A | 2/1981 | Herczog et al. | |
| 4,326,529 A | 4/1982 | Doss et al. | |
| 4,381,007 A | 4/1983 | Doss | |
| 4,476,862 A | 10/1984 | Pao | |
| 4,532,924 A | 8/1985 | Auth et al. | |
| 4,548,207 A | 10/1985 | Reimels | |
| 4,567,890 A | 2/1986 | Ohta et al. | |
| 4,590,934 A | 5/1986 | Malis et al. | |
| 4,593,691 A | 6/1986 | Lindstrom et al. | |
| 4,658,817 A | 4/1987 | Hardy | |
| 4,660,571 A | 4/1987 | Hess et al. | |
| 4,674,499 A | 6/1987 | Pao | |
| 4,682,596 A | 7/1987 | Bales et al. | |
| 4,706,667 A | 11/1987 | Roos | |
| 4,727,874 A | 3/1988 | Bowers et al. | |
| 4,736,743 A | 4/1988 | Daikuzono | |
| 4,737,678 A | 4/1988 | Hasegawa | |
| 4,762,128 A | 8/1988 | Rosenbluth | |
| 4,765,331 A | 8/1988 | Petruzzi et al. | |
| 4,785,806 A | 11/1988 | Deckelbaum | |
| 4,785,823 A | 11/1988 | Eggers et al. | |
| 4,799,480 A | 1/1989 | Abraham et al. | |
| 4,805,616 A | 2/1989 | Pao | |
| 4,823,791 A | 4/1989 | D'Amelio et al. | |
| 4,832,048 A | 5/1989 | Cohen | |
| 4,920,978 A | 5/1990 | Colvin | |
| 4,931,047 A | 6/1990 | Broadwin et al. | |
| 4,936,281 A | 6/1990 | Stasz | |
| 4,936,301 A | 6/1990 | Rexroth et al. | |
| 4,943,290 A | 7/1990 | Rexroth et al. | |
| 4,966,597 A | 10/1990 | Cosman | |
| 4,967,765 A | 11/1990 | Turner et al. | |
| 4,968,314 A | 11/1990 | Michaels | |
| 4,976,711 A | 12/1990 | Parins et al. | |
| 4,979,948 A | 12/1990 | Geddes et al. | |
| 4,998,933 A | 3/1991 | Eggers et al. | |
| 5,007,437 A | 4/1991 | Sterzer | |
| 5,007,908 A | 4/1991 | Rydell | |
| 5,009,656 A | 4/1991 | Reimels | |
| 5,035,696 A | 7/1991 | Rydell | |
| 5,037,421 A | 8/1991 | Boutacoff et al. | |
| 5,047,026 A | 9/1991 | Rydell | |
| 5,047,027 A | 9/1991 | Rydell | |
| 5,059,192 A | 10/1991 | Zaias | |
| 5,061,266 A | 10/1991 | Hakky | |
| 5,065,515 A | 11/1991 | Iderosa | |
| 5,078,717 A | 1/1992 | Parins et al. | |
| 5,080,660 A | 1/1992 | Buelna | |
| 5,084,044 A | 1/1992 | Quint | |
| 5,085,659 A | 2/1992 | Rydell | |
| 5,088,997 A | 2/1992 | Delahuerga et al. | |
| 5,098,431 A | 3/1992 | Rydell | |
| 5,099,840 A | 3/1992 | Goble | |
| 5,102,410 A | 4/1992 | Dressel | |
| 5,108,391 A | 4/1992 | Flachenecker et al. | |
| 5,112,330 A | 5/1992 | Nishigaki et al. | |
| 5,122,138 A | 6/1992 | Manwaring | |
| 5,125,928 A | 6/1992 | Parins et al. | |
| 5,143,063 A | 9/1992 | Fellner | |
| 5,147,354 A | 9/1992 | Boutacoff | |
| 5,167,659 A | 12/1992 | Ohtomo et al. | |
| 5,171,311 A | 12/1992 | Rydell et al. | |
| 5,178,620 A | 1/1993 | Eggers et al. | |
| 5,182,857 A | 2/1993 | Simon | |
| 5,190,517 A | 3/1993 | Zieve et al. | |
| 5,192,280 A | 3/1993 | Parins | |
| 5,195,959 A | 3/1993 | Smith | |
| 5,197,466 A | 3/1993 | Marchosky et al. | |
| 5,197,963 A | 3/1993 | Parins | |
| 5,207,675 A | 5/1993 | Canady | |
| 5,217,455 A | 6/1993 | Tan | |
| 5,217,457 A | 6/1993 | Delahuerga et al. | |
| 5,217,459 A | 6/1993 | Kamerling | |
| 5,226,907 A | 7/1993 | Tankovich | |
| 5,231,984 A | 8/1993 | Santana-Blank | |
| 5,241,972 A | 9/1993 | Bonati | |
| 5,261,410 A | 11/1993 | Alfano et al. | |
| 5,267,994 A | 12/1993 | Gentelia et al. | |
| 5,267,997 A | 12/1993 | Farin et al. | |
| 5,273,524 A | 12/1993 | Fox et al. | |
| 5,277,201 A | 1/1994 | Stern | |
| 5,287,380 A | 2/1994 | Hsia | |
| 5,290,273 A | 3/1994 | Tan | |
| 5,290,282 A | 3/1994 | Casscells | |
| 5,300,069 A | 4/1994 | Hunsberger et al. | |
| 5,300,099 A | 4/1994 | Rudie | |
| 5,301,687 A | 4/1994 | Wong et al. | |
| 5,304,169 A | 4/1994 | Sand | |
| 5,304,170 A | 4/1994 | Green | |
| 5,306,238 A | 4/1994 | Fleenor | |
| 5,312,395 A | 5/1994 | Tan et al. | |
| 5,312,400 A | 5/1994 | Bales et al. | |
| 5,314,406 A | 5/1994 | Arias et al. | |
| 5,320,618 A | 6/1994 | Gustafsson | |
| 5,322,507 A | 6/1994 | Costello et al. | |
| 5,324,254 A | 6/1994 | Phillips | |
| 5,329,943 A | 7/1994 | Johnson | |
| 5,330,470 A | 7/1994 | Hagen | |
| 5,330,518 A | 7/1994 | Neilson et al. | |
| 5,334,140 A | 8/1994 | Phillips | |
| 5,336,217 A | 8/1994 | Buys et al. | |
| 5,342,357 A | 8/1994 | Nardella | |
| 5,360,447 A | 11/1994 | Koop | |
| 5,366,443 A | 11/1994 | Eggers et al. | |
| 5,370,642 A | 12/1994 | Keller | |
| 5,370,675 A | 12/1994 | Edwards et al. | |
| 5,375,588 A | 12/1994 | Yoon | |
| 5,380,277 A | 1/1995 | Phillips | |
| 5,380,316 A | 1/1995 | Aita et al. | |
| 5,383,876 A | 1/1995 | Nardella | |
| 5,383,917 A | 1/1995 | Desai et al. | |
| 5,389,096 A | 2/1995 | Aita et al. | |
| 5,395,312 A | 3/1995 | Desai | |
| 5,417,687 A | 5/1995 | Nardella et al. | |
| 5,419,767 A | 5/1995 | Eggers et al. | |
| 5,423,803 A | 6/1995 | Tankovich et al. | |
| 5,423,810 A | 6/1995 | Goble et al. | |
| 5,423,883 A | 6/1995 | Helland | |
| 5,425,728 A | 6/1995 | Tankovich | |
| 5,433,708 A | 7/1995 | Nichols et al. | |
| 5,436,566 A | 7/1995 | Thompson et al. | |
| 5,438,302 A | 8/1995 | Goble | |
| 5,441,499 A | 8/1995 | Fritzsch | |
| 5,445,634 A | 8/1995 | Keller | |
| 5,449,378 A | 9/1995 | Schouenborg | |
| 5,451,224 A | 9/1995 | Goble et al. | |
| 5,454,809 A | 10/1995 | Janssen | |

| | | |
|---|---|---|
| 5,484,435 A | 1/1996 | Fleenor et al. |
| 5,490,850 A | 2/1996 | Ellman et al. |
| 5,496,312 A | 3/1996 | Klicek |
| 5,496,314 A | 3/1996 | Eggers |
| 5,496,317 A | 3/1996 | Goble et al. |
| 5,507,790 A | 4/1996 | Weiss |
| 5,514,130 A * | 5/1996 | Baker .......................... 606/41 |
| 5,522,813 A | 6/1996 | Trelles |
| 5,556,397 A * | 9/1996 | Long et al. .................... 606/48 |
| 5,569,242 A | 10/1996 | Lax et al. |
| 5,571,100 A | 11/1996 | Goble et al. |
| 5,578,029 A | 11/1996 | Trelles et al. |
| 5,584,872 A | 12/1996 | LaFontaine et al. |
| 5,609,151 A | 3/1997 | Mulier et al. |
| 5,633,578 A | 5/1997 | Eggers et al. |
| 5,647,869 A | 7/1997 | Goble et al. |
| 5,660,836 A | 8/1997 | Knowlton |
| 5,662,680 A | 9/1997 | Desai |
| 5,676,693 A | 10/1997 | LaFontaine et al. |
| 5,681,282 A | 10/1997 | Eggers et al. |
| 5,683,366 A | 11/1997 | Eggers et al. |
| 5,683,386 A | 11/1997 | Ellman et al. |
| 5,683,387 A | 11/1997 | Garito et al. |
| 5,695,495 A | 12/1997 | Ellman et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,725,524 A | 3/1998 | Mulier et al. |
| 5,746,746 A | 5/1998 | Garito et al. |
| 5,766,153 A | 6/1998 | Eggers et al. |
| 5,807,395 A | 9/1998 | Mulier et al. |
| 5,810,764 A | 9/1998 | Eggers et al. |
| 5,810,809 A | 9/1998 | Rydell |
| 5,843,019 A | 12/1998 | Eggers et al. |
| 5,843,078 A * | 12/1998 | Sharkey ........................ 606/41 |
| 5,860,951 A | 1/1999 | Eggers et al. |
| 5,860,975 A | 1/1999 | Goble et al. |
| 5,871,469 A | 2/1999 | Eggers et al. |
| 5,873,855 A | 2/1999 | Eggers et al. |
| 5,885,277 A | 3/1999 | Korth |
| 5,888,198 A | 3/1999 | Eggers et al. |
| 5,891,095 A | 4/1999 | Eggers et al. |
| 5,897,553 A * | 4/1999 | Mulier et al. .................. 606/41 |
| 5,902,272 A | 5/1999 | Eggers et al. |
| 5,931,807 A | 8/1999 | McClure et al. |
| 5,944,715 A | 8/1999 | Goble et al. |
| 5,948,011 A | 9/1999 | Knowlton |
| 6,004,319 A | 12/1999 | Goble et al. |
| 6,013,076 A | 1/2000 | Goble et al. |
| 6,015,406 A | 1/2000 | Goble et al. |
| 6,024,733 A * | 2/2000 | Eggers et al. ................ 604/114 |
| 6,027,501 A | 2/2000 | Goble et al. |
| 6,039,734 A | 3/2000 | Goble |
| 6,047,215 A | 4/2000 | McClure et al. |
| 6,056,746 A | 5/2000 | Goble et al. |
| 6,063,079 A | 5/2000 | Hovda et al. |
| 6,066,134 A | 5/2000 | Eggers et al. |
| 6,068,628 A | 5/2000 | Fanton et al. |
| 6,074,386 A | 6/2000 | Goble et al. |
| 6,090,106 A | 7/2000 | Goble et al. |
| 6,093,186 A | 7/2000 | Goble et al. |
| 6,102,046 A | 8/2000 | Weinstein et al. |
| 6,109,268 A | 8/2000 | Thapliyal et al. |
| 6,117,109 A * | 9/2000 | Eggers et al. ................ 604/114 |
| 6,126,682 A | 10/2000 | Sharkey et al. |
| 6,142,992 A | 11/2000 | Cheng et al. |
| 6,149,620 A | 11/2000 | Baker et al. |
| 6,159,194 A | 12/2000 | Eggers et al. |
| 6,159,208 A | 12/2000 | Hovda et al. |
| 6,168,593 B1 | 1/2001 | Sharkey et al. |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,203,542 B1 | 3/2001 | Ellsberry et al. |
| 6,210,402 B1 * | 4/2001 | Olsen et al. ................. 604/114 |
| 6,224,592 B1 | 5/2001 | Eggers et al. |
| 6,228,081 B1 | 5/2001 | Goble |
| 6,235,020 B1 | 5/2001 | Cheng et al. |
| 6,238,391 B1 | 5/2001 | Olsen et al. |
| 6,254,600 B1 | 7/2001 | Willink et al. |
| 6,261,286 B1 | 7/2001 | Goble et al. |
| 6,264,652 B1 | 7/2001 | Eggers et al. |
| 6,277,112 B1 | 8/2001 | Underwood et al. |
| 6,277,116 B1 | 8/2001 | Utely et al. |
| 6,293,942 B1 | 9/2001 | Goble et al. |
| 6,296,636 B1 | 10/2001 | Cheng et al. |
| 6,296,638 B1 | 10/2001 | Davison et al. |
| 6,306,134 B1 | 10/2001 | Goble et al. |
| 6,312,408 B1 | 11/2001 | Eggers et al. |
| 6,322,549 B1 | 11/2001 | Eggers et al. |
| 6,355,032 B1 | 3/2002 | Hovda et al. |
| 6,363,937 B1 | 4/2002 | Hovda et al. |
| 6,379,351 B1 | 4/2002 | Thapliyal et al. |
| 6,391,025 B1 | 5/2002 | Weinstein et al. |
| 6,416,507 B1 | 7/2002 | Eggers et al. |
| 6,416,508 B1 | 7/2002 | Eggers et al. |
| 6,432,103 B1 | 8/2002 | Ellsberry et al. |
| 6,468,274 B1 | 10/2002 | Alleyne et al. |
| 6,530,922 B1 | 3/2003 | Cosman et al. |
| 6,602,248 B1 | 8/2003 | Sharps et al. |
| 6,632,193 B1 | 10/2003 | Davison et al. |
| 6,632,220 B1 | 10/2003 | Eggers et al. |
| 2002/0029036 A1 | 3/2002 | Goble et al. |
| 2002/0120260 A1 | 8/2002 | Morris et al. |

FOREIGN PATENT DOCUMENTS

| | | | |
|---|---|---|---|
| EP | 0 754 437 | 1/1997 | ........... A61B/17/39 |
| EP | 0 694 290 | 11/2000 | ........... A61B/18/04 |
| FR | 2313949 | 1/1977 | ........... A61N/3/02 |
| GB | 2 308 979 | 7/1997 | ........... A61B/17/36 |
| GB | 2 308 980 | 7/1997 | ........... A61B/17/36 |
| GB | 2 327 350 | 1/1999 | ........... A61B/17/39 |
| GB | 2 327 351 | 1/1999 | ........... A61B/17/39 |
| GB | 2 327 352 | 1/1999 | ........... A61B/17/39 |
| JP | 57-57802 | 4/1982 | ........... A61B/1/00 |
| JP | 570117843 | 7/1982 | ........... A61B/17/39 |
| WO | 90/03152 | 4/1990 | ........... A61B/17/39 |
| WO | WO 90/07303 | 7/1990 | ........... A61B/17/39 |
| WO | 92/21278 | 12/1992 | ........... A61B/5/04 |
| WO | WO 93/13816 | 7/1993 | ........... A61B/17/36 |
| WO | 93/20747 | 10/1993 | ........... A61B/5/00 |
| WO | WO 94/04220 | 3/1994 | |
| WO | 94/08654 | 4/1994 | ........... A61M/37/00 |
| WO | WO 95/34259 | 12/1995 | ........... A61F/5/48 |
| WO | 96/00042 | 1/1996 | ........... A61B/17/39 |
| WO | 97/00646 | 1/1997 | ........... A61B/17/39 |
| WO | 97/00647 | 1/1997 | ........... A61B/17/39 |
| WO | 97/15238 | 5/1997 | |
| WO | 97/24073 | 7/1997 | ........... A61B/17/39 |
| WO | WO 97/24074 | 7/1997 | ........... A61B/17/39 |
| WO | 97/24993 | 7/1997 | ........... A61B/17/39 |
| WO | 97/24994 | 7/1997 | ........... A61B/17/39 |
| WO | 97/48345 | 12/1997 | ........... A61B/17/39 |
| WO | 97/48346 | 12/1997 | ........... A61B/17/39 |
| WO | 98/07468 | 2/1998 | ........... A61N/1/40 |
| WO | 98/27879 | 7/1998 | ........... A61B/17/36 |
| WO | 98/27880 | 7/1998 | ........... A61B/17/39 |
| WO | 98/44968 | 10/1998 | |
| WO | 99/51155 | 10/1999 | ........... A61B/17/36 |

| | | | |
|---|---|---|---|
| WO | 99/51158 | 10/1999 | A61B/17/39 |

OTHER PUBLICATIONS

R. Tucker et al., Abstract P14–11, p. 248, "A Bipolar Electrosurgical Turp Loop".

R. Tucker et al., *J. of Urology* vol. 141, pp. 662–665, (1989).

R. Tucker et al. *Urological Research* vol. 18, pp. 291–294 (1990).

Kramolowsky et al. *J. of Urology* vol. 143, pp. 275–277 (1990).

Kramolowsky et al., *J. of Urology* vol. 146, pp. 669–674 (1991).

Slager et al. *Z. Kardiol.* 76: Suppl. 6, 67–71 (1987).

Slager et al. *JACC* 5(6):1382–6 (1985).

Olsen MD, Bipolar Laparoscopic Cholecstectomy Lecture (marked confidential), Oct. 7, 1991.

Codman & Shurtleff, Inc. "The Malis Bipolar Electrosurgical System CMC–III Instruction Manual" Jul. 1991.

Valley Forge's New Products, CLINICA, 475, 5, Nov. 6, 1991.

Valley Forge Scientific Corp., "Summary of Safety and Effective Information from 510K," 1991.

Codman & Shurtleff, Inc. "The Malis Bipolar coagulating and Bipolar Cutting System CMC–II" brochure, early 1991.

L. Malis, "The Value of Irrigation During Bipolar Coagulation" see ARTC 21602, early Apr. 9, 1993.

L. Malis, "Excerpted from a seminar by Leonard I. Malis, M.D. at the 1995 American Association of Neurological Surgeons Meeting," 1995.

L. Malis, "Electrosurgery, Technical Note," *J. Neursurg.*, vol. 85, 970–975, Nov. 1996.

Ian E. Shuman, "Bipolar Versus Monopolar Electrosurgery: Clinical Applications," *Dentistry Today*, vol. 20, No. 12, Dec. 2001.

Protell et al., "Computer–Assisted Electrocoagulation: Bipolar v. Monopolar in the Treatment of Experimental Canine Gastric Ulcer Bleeding," *Gastroenterology* vol. 80, No. 3, pp. 451–455.

Cook and Webster, "Therapeutic Medical Devices: Application and Design," 1982.

Valleylab SSE2L Instruction Manual, Jan. 6, 1983.

Robert D. Tucker et al., "Demodulated Low Frequency Currents from Electrosurgical Procedures," *Surgery, Gynecology and Obstetrics*, 159:39–43, 1984.

Lu, et al., "Electrical Thermal Angioplasty: Catheter Design Features, In Vitro Tissue Ablation Studies and In Vitro Experimental Findings," *Am J. Cardiol* vol. 60, pp. 1117–1122.

Selikowitz & LaCourse, "Electric Current and Voltage Recordings on the Myocardium During Electrosurgical Procedures in Canines," *Surgery, Gynecology & Obstetrics*, vol. 164, 219–224, Mar. 1987.

J. O'Malley, Schaum's Outline of Theory and Problems of Basic Circuit Analysis, McGraw–Hill, $2^{nd}$ Ed., 1992, pp. 3–5.

Arnaud Wattiez et al., "Electrosurgery in Operative Endoscopy," Electrosurgical Effects, Blackwell Science, pp. 85–93, 1995.

Leslie A. Geddes, "Medical Device Accidents: With Illustrative Cases" CRC Press, 1998.

Wyeth, "Electrosurgical Unit" pp. 1181–1202.

C.P. Swain, et al., *Gut* vol. 25, pp. 1424–1431 (1984).

Piercey et al., *Gastroenterology* vol. 74(3), pp. 527–534 (1978).

A.K. Dobbie *Bio–Medical Engineering* vol. 4, pp. 206–216 (1969).

B. Lee et al. JACC vol. 13(5), pp. 1167–1175 (1989).

K. Barry et al., *American Heart Journal* vol. 117, pp. 332–341 (1982).

W. Honig *IEEE* pp. 58–65 (1975).

Jacob Kline, *Handbook of Biomedical Engineering*, Academic Press Inc., N.Y., pp. 98–113, 1988.

M.B. Dennis et al. "Evolution of Electrofulguration in Control of Bleeding of Experimental Gastric Ulcers," Digestive Diseases and Sciences, vol. 24, No. 11, 845–848.

Letter from Department of Health to Jerry Malis dated Apr. 15, 1985.

Letter from Jerry Malis to FDA dated Jul. 25, 1985.

Letter from Department of Health to Jerry Malis dated Apr. 22, 1991.

Leonard Malis, "Instrumentation for Microvascular Neurosurgery" *Cerebrovascular Surgery*, vol. 1, 245–260, 1985.

Valleylab, Inc. "Valleylab Part No. 945 100 102 A" Surgistat Service Manual, Jul. 1988.

Leonard I. Malis, "New Trends in Microsurgery and Applied Technology," *Advanced Technology in Neurosurgery*, 1–16, 1988.

\* cited by examiner

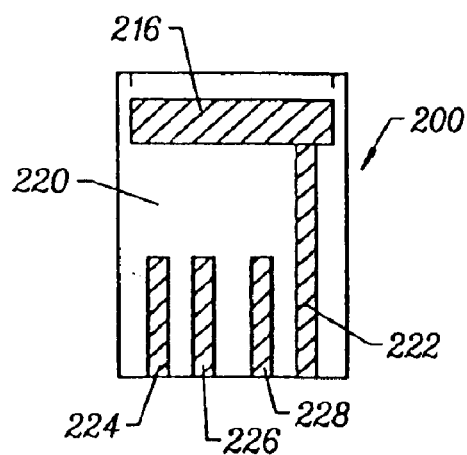
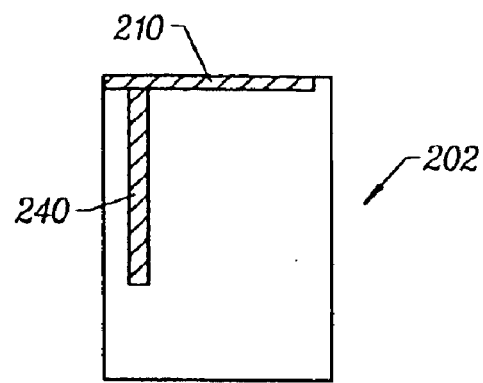
FIG. 9A          FIG. 10A
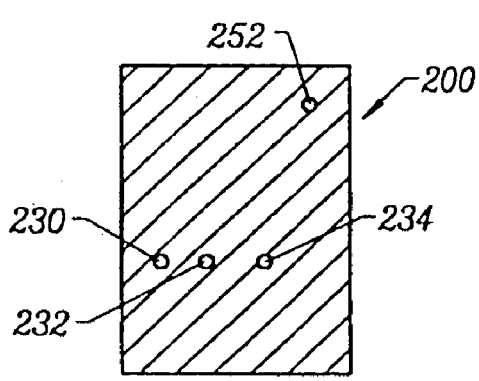
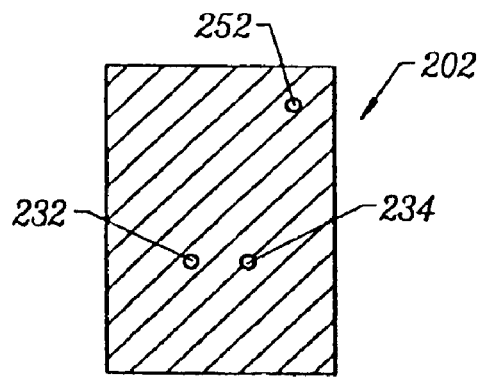
FIG. 9B          FIG. 10B

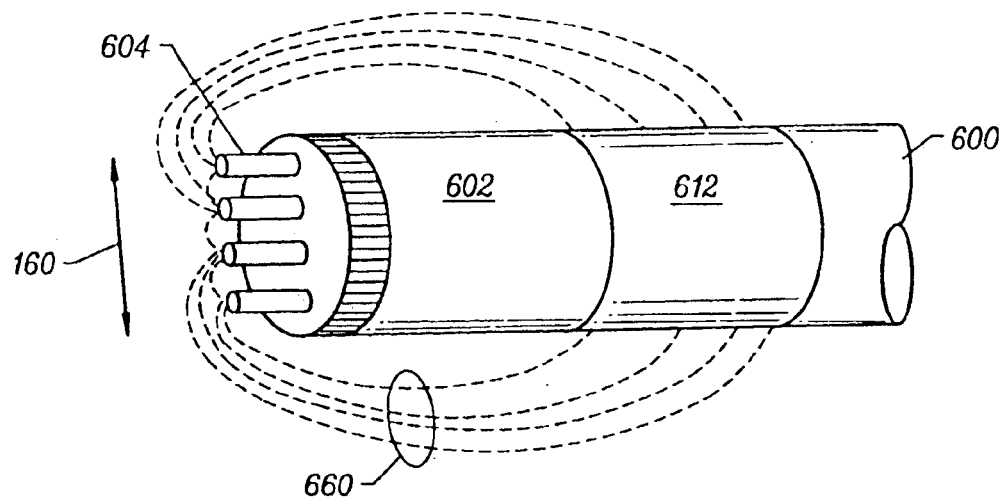
FIG. 27
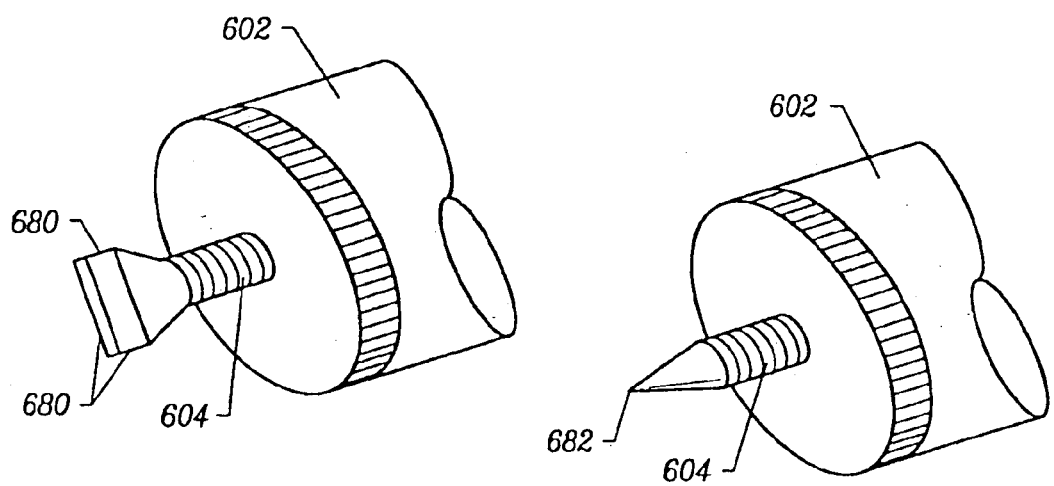
FIG. 28
FIG. 29

METHODS FOR ELECTROSURGICAL INCISIONS ON EXTERNAL SKIN SURFACES

RELATED APPLICATIONS

The present invention is a division of U.S. patent application Ser. No. 09/162,117, filed Sep. 28, 1998, now U.S. Pat. No. 6,117,109, which is a continuation-in-part of U.S. patent application Ser. No. 08/977,845, filed Nov. 25, 1997 now U.S. Pat. No. 6,210,402, which is a continuation-in-part of application Ser. No. 08/562,332, filed Nov. 22, 1995 now U.S. Pat. No. 6,024,733, the complete disclosures of which are incorporated herein by reference for all purposes.

The present invention is related to commonly assigned co-pending U.S. patent application Ser. No. 08/990,374, filed Dec. 15, 1997, which is a continuation-in-part of U.S. patent application Ser. No. 08/485,219, filed on Jun. 7, 1995, now U.S. Pat. No. 5,697,281, patent application Ser. Nos. 09/109,219, 09/058,571, 08/874,173 and 09/002,315, filed on Jun. 30, 1998, Apr. 10, 1998, Jun. 13, 1997, and Jan. 2, 1998, respectively and U.S. patent application Ser. No. 09/054,323, filed on Apr. 2, 1998, U.S. patent application Ser. No. 09/010,382, filed Jan. 21, 1998 and U.S. patent application Ser. No. 09/032,375, filed Feb. 27, 1998, U.S. patent application Ser. Nos. 08/977,845, filed on Nov. 25, 1997 08/942,580, filed on Oct. 2, 1997, U.S. application Ser. No. 08/753,227, filed on Nov. 22, 1996, U.S. application Ser. No. 08/687,792, filed on Jul. 18, 1996, and PCT International Application, U.S. National Phase Ser. No. PCT/US94/05168, filed on May 10, 1994, now U.S. Pat. No. 5,697,909, which was a continuation-in-part of U.S. patent application Ser. No. 08/059,681, filed on May 10, 1993, which was a continuation-in-part of U.S. patent application Ser. No. 07/958,977, filed on Oct. 9, 1992 which was a continuation-in-part of U.S. patent application Ser. No. 07/817,575, filed on Jan. 7, 1992, the complete disclosures of which are incorporated herein by reference for all purposes. The present invention is also related to commonly assigned U.S. Pat. No. 5,683,366, filed Nov. 22, 1995, the complete disclosure of which is incorporated herein by reference for all purposes.

BACKGROUND OF THE INVENTION

The present invention relates generally to the field of electrosurgery, and more particularly to surgical devices and methods which employ high frequency electrical energy to treat a patient's skin and subcutaneous tissue, including skin resurfacing procedures, the removal of pigmentations, vascular lesions, scars and tattoos, hair removal and/or transplant procedures, treatment of skin cancer, skin rejuvenation (e.g., wrinkle removal), liposuction, blepharoplasty and the like.

In early dermatology procedures, cosmetic surgeons often employed chemical peels and/or dermabrasion techniques to remove outer layers of the patient's skin to rejuvenate wrinkled skin or to remove skins disorders, such as acne, lesions, early skin cancer, etc. These dermabrasion and chemical procedures, however, are difficult to control, requiring great surgical skill. In addition, these somewhat inelegant techniques often cause excessive bleeding, collateral tissue damage and patient discomfort.

In an effort to overcome some of the limitations of dermabrasion and chemical peels, lasers have been developed for use in cosmetic surgery. Lasers have improved the accuracy of skin resurfacing procedures, and they have reduced collateral damage to the tissue surrounding and underlying the treatment site. In laser dermatology applications, a handpiece is typically used to guide the output of a laser to the patient's skin, and to form a laser spot of a desired size on the region of the skin which is to be treated. The handpiece is typically attached to one end of an articulated arm which transmits the output of a medical laser (such as $CO_2$ or Er: YAG lasers) to the handpiece and allows the handpiece a wide range of motion.

Although initially promising, lasers suffer from a number of drawbacks in dermatology procedures. In the first place, laser equipment can be very expensive because of the costs associated with the laser light sources. Moreover, those lasers which permit acceptable depths of necrosis (such as excimer lasers, erbium:YAG lasers, and the like) provide a very low volumetric ablation rate, requiring numerous passes over the same treatment area which amounts to longer procedural times. In addition, erbium:YAG lasers generally do not provide effective hemostasis during the procedure, resulting in excessive bleeding which disrupts the surgeon's view of the treatment site. The $CO_2$ lasers provide a higher rate of ablation and an increased depth of tissue necrosis than their erbium: YAG counterparts. On the other hand, $CO_2$ lasers often create significant residual thermal injury to tissue at and surrounding the treatment site, which requires long healing periods for the patient. In addition, $CO_2$ lasers are associated with much pain and, therefore, require a lot of anesthesia, which increases the cost and length of the procedure.

In the treatment of vascular lesions, lasers are used to irradiate the surface of the skin. The laser energy penetrates through the skin and is absorbed in the blood, which coagulates and collapses the vein. Unfortunately, there are also problems associated with the use of lasers in these procedures. For example, although most of the laser energy passes through the tissue to the vessel, scattering and absorption of the light take place in the tissue. This absorption can cause significant changes in skin coloration and even scarring.

Monopolar electrosurgical instruments have been used to effect electro-dessication of abnormalities, such as lesions, skin tags, viral warts, pigment nevi, moles and skin cancer. For example, Conmed Corporation manufacturers a monopolar device, termed the Hyfrecator™ having a single active electrode at the tip of an electrosurgical probe. In these procedures, the skin abnormality is typically removed with a scalpel, and a low voltage is applied to the active electrode in contact with the target tissue to deliver electric current through the tissue and the patient to a dispersive pad or indifferent electrode. The voltage desiccates the remaining abnormal tissue, and coagulates severed blood vessels at the target site. The remaining tissue is then removed with a sponge or similar material. The voltage generally must be low enough to prevent charring and potential scarring of the underlying dermis.

The present invention is particularly concerned with treating "baggy eyelids" deformity, a condition that can result in both functional and cosmetic problems. Baggy eyelids can be caused by a variety of conditions, such as blepharochalasis (laxity and sagging of the upper eyelid), dermatochalasis (loss of skin elasticity in the upper eyelid), hypertrophy of the orbicularis muscle, protrusion of intraorbit fat and lateral fullness of the upper eye. Surgical treatment for baggy eyelids, known as blepharoplasty, typically involves the creation of a linear or crescent shaped incision across the upper or lower eyelid so that a portion of the patient's skin can be folded over to expose the underlying orbital septum. The orbital septum is then opened to expose the underlying fat tissue, and the desired amount of fat tissue is excised from the patient.

The dermal incisions required to expose underlying fatty tissue are typically created with a variety of convention resection devices, such as a scalpel or laser. While generally effective, these devices each have one or more drawbacks. The scalpel requires additional hemostasis, and often leads to postoperative pain and relatively long healing periods. Lasers typically effect simultaneous hemostasis as they deliver thermal energy to the target area. However, this thermal energy also leads to excess healing time and postoperative pain. In addition, the amount of thermal energy required by these devices may sufficient damage the target site to leave a permanent scar on the patient.

RF energy has been used to remove or otherwise treat tissue in open and endoscopic procedures since they generally reduce patient bleeding associated with tissue cutting operations and improve the surgeon's visibility. In procedures for treating baggy eyelids, monopolar RF devices, e.g., the Colorado Needle™, are frequently used to create the necessary incisions in the patient's eyelids. These electrosurgical devices and procedures, however, suffer from a number of disadvantages. For example, conventional electrosurgical cutting devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. This cutting effect generally results in the production of smoke, or an electrosurgical plume, which can spread bacterial or viral particles from the tissue to the surgical team or to other portions of the patient's body. In addition, the tissue is parted along the pathway of evaporated cellular fluid, inducing undesirable collateral tissue damage in regions surrounding the target tissue site.

SUMMARY OF THE INVENTION

The present invention provides systems, apparatus and methods for selectively applying electrical energy to the epidermis, dermis or underlying subcutaneous tissue of a patient. The systems and methods of the present invention are particularly useful for creating precise incisions in external skin surfaces, such as the face, with minimal pain and postoperative scarring.

In one aspect of the invention, a method for removing fatty tissue underlying a patient's epidermis is disclosed (e.g., blepharoplasty, brow lifts, eyelid shortening procedures, and the like). This method includes positioning one or more active electrode(s) and one or more return electrode(s) in close proximity to a target site on an external body surface of the patient. A high frequency voltage difference is applied between the active and return electrode (s), and the active electrode(s) are translated across the external body surface to-create an incision therein. The bipolar configuration of the present invention controls the flow of current to the immediate region around the distal end of the probe, which minimizes tissue necrosis and the conduction of current through the patient. The residual heat from the electrical energy also provides simultaneous hemostasis of severed blood vessels, which increases visualization and improves recovery time for the patient. The techniques of the present invention produce significantly less thermal energy than many conventional techniques, such as lasers and conventional RF devices, which reduces collateral tissue damage and minimizes pain and postoperative scarring.

In some procedures, such as blepharoplasty, the incision will be selected to allow a portion of external skin to be removed (i.e., folded over or removed entirely) to expose the underlying tissue, such as the orbital septum in blepharoplasty procedures. Depending on the specific procedure, the fatty portions of the underlying tissue are then removed either with conventional tools, such as a scalpel, or with the electrosurgical instruments described herein. In the latter embodiment, a sufficient high frequency voltage is applied between the active and return electrode(s) to volumetrically remove this fatty tissue either in situ, or by breaking up the tissue sufficiently to enable removal by suction pressure (e.g., liposuction). In this latter case, the tissue may be removed by an electrosurgical probe having an aspiration lumen and/or an aspiration electrode to prevent clogging of the lumen. A more complete description of such a device can be found in Ser. No. 09/010,382, filed Jan. 21, 1998 previously incorporated herein by reference.

The return electrode(s) are preferably spaced from the active electrode(s) a sufficient distance to prevent arcing therebetween at the voltages suitable for tissue removal, and to prevent contact of the return electrode(s) with the tissue. The current flow path between the active and return electrodes may be generated by directing an electrically conducting fluid along a fluid path past the return electrode and to the target site, or by locating a viscous electrically conducting fluid, such as a gel, at the target site, and submersing the active and return electrode(s) within the conductive gel. The electrically conductive fluid will be selected to have sufficient electrical conductivity to allow current to pass therethrough from the active to the return electrode, and such that the fluid ionizes into a plasma when subject to sufficient electrical energy, as discussed below. In the exemplary embodiment, the conductive fluid is isotonic saline, although other fluids may be selected.

In the exemplary embodiment, the incision is created by removing tissue with molecular dissociation or disintegration processes. Conventional electrosurgery cuts through tissue by rapidly heating the tissue until cellular fluids explode, producing a cutting effect along the pathway of localized heating. The present invention volumetrically removes the tissue along the cutting pathway in a cool ablation process that minimizes thermal damage to surrounding tissue. In these processes, the high frequency voltage applied to the active electrode(s) is sufficient to vaporize an electrically conductive fluid (e.g., gel or saline) between the electrode(s) and the tissue. Within the vaporized fluid, a ionized plasma is formed and charged particles (e.g., electrons) are accelerated towards the tissue to cause the molecular breakdown or disintegration of several cell layers of the tissue. This molecular dissociation is accompanied by the volumetric removal of the tissue. The short range of the accelerated charged particles within the plasma layer confines the molecular dissociation process to the surface layer to minimize damage and necrosis to the underlying tissue. This process can be precisely controlled to effect the volumetric removal of tissue as thin as 10 to 50 microns with minimal heating of, or damage to, surrounding or underlying tissue structures. A more complete description of this phenomena is described in commonly assigned U.S. Pat. No. 5,683,366, the complete disclosure of which is incorporated herein by reference.

The present invention offers a number of advantages over current RF and laser techniques for creating incisions in skin. The ability to precisely control the volumetric removal of tissue results in a field of tissue cutting or removal that is very defined, consistent and predictable. Controlling the depth of tissue removal allows the physician to form a precise incision through the skin tissue. This precise heating also helps to minimize or completely eliminate damage to healthy tissue structures or nerves that are often adjacent to the target tissue. In addition, small blood vessels within the skin tissue are simultaneously cauterized and sealed as the tissue is removed to continuously maintain hemostasis during the procedure. This increases the surgeon's field of view, and shortens the length of the procedure. Moreover, since the present invention allows for the use of electrically conductive fluid (contrary to prior art bipolar and monopolar electrosurgery techniques), isotonic saline may be used during the procedure. Saline is the preferred medium for irrigation because it has the same concentration as the body's fluids and, therefore, is not absorbed into the body as much as other fluids.

Apparatus according to the present invention generally include an electrosurgical probe or handpiece having a shaft or handle with proximal and distal ends and an electrode assembly at the distal end. The apparatus will preferably further include a fluid delivery element for delivering electrically conducting fluid to the electrode terminal(s) and the target site. The fluid delivery element may be located on the probe, e.g., a fluid lumen or tube, or it may be part of a separate instrument. Alternatively, an electrically conducting gel or spray, such as a saline electrolyte or other conductive gel, may be applied to the target site. In this embodiment, the apparatus may not have a fluid delivery element. In both embodiments, the electrically conducting fluid will preferably generate a current flow path from the electrode terminals to one or more return electrode(s). In an exemplary embodiment, the return electrode is located on the probe and spaced a sufficient distance from the electrode terminal(s) to substantially avoid or minimize current shorting therebetween and to shield the return electrode from tissue at the target site.

In a specific configuration, the electrode assembly comprises an active electrode spaced from a return electrode by an electrically insulating electrode support member. In an exemplary embodiment, the active electrode has a substantially elongate shape with a sharp distal end to facilitate the cutting or incision of tissue, usually having a width of about 0.01 mm to 10 mm, preferably about 0.1 to 0.5 mm and an exposed length of about 5 to 50 mm, preferably about 10 to 30 mm. The return electrode comprises an electrically conductive sleeve surrounding the insulating support member, which extends distally therefrom. Likewise, the support member preferably comprises an insulating sleeve surrounding the active electrode which extends distally therefrom. In the exemplary embodiment, the electrode assembly extends from the distal face of a support member or disposable tip, which may be attached to a handle to facilitate use by the surgeon. The disposable tip typically includes a fluid lumen having a distal opening adjacent to the electrode assembly for delivery of electrically conductive fluid to the target site. In the preferred embodiment, the fluid lumen extends through the disposable tip, although it may also comprises a fluid tube that extends on the exterior of the tip.

In an alternative embodiment, an electrosurgical probe includes one or more electrode terminal(s) designed for cutting tissue; i.e., they typically have a distal edge or point. In this embodiment, the electrode terminal(s) are aligned with each other to form a linear cutting path through the tissue. The return electrode preferably comprises a conductive sleeve on the shaft spaced proximally from the electrode terminal(s). The conductive sleeve may be a separate conductive element attached to an insulating shaft, or an exposed portion of a conductive shaft.

A further understanding of the nature and advantages of the invention will become apparent by reference to the remaining portions of the specification and drawings.

BRIEF DESCRIPTION OF THE DRAWINGS

FIGS. 9A–13 are side views of the individual wafer layers of the electrode support;

FIGS. 9B–12B are cross-sectional views of the individual wafer layers;

FIG. 27 is a detailed end view of an electrosurgical probe having an elongate, linear array of electrode terminals suitable for use in surgical cutting;

FIG. 28 is a detailed view of a single electrode terminal having a flattened end at its distal tip;

FIG. 29 is a detailed view of a single electrode terminal having a pointed end at its distal tip;

DESCRIPTION OF SPECIFIC EMBODIMENTS

Figure 1:
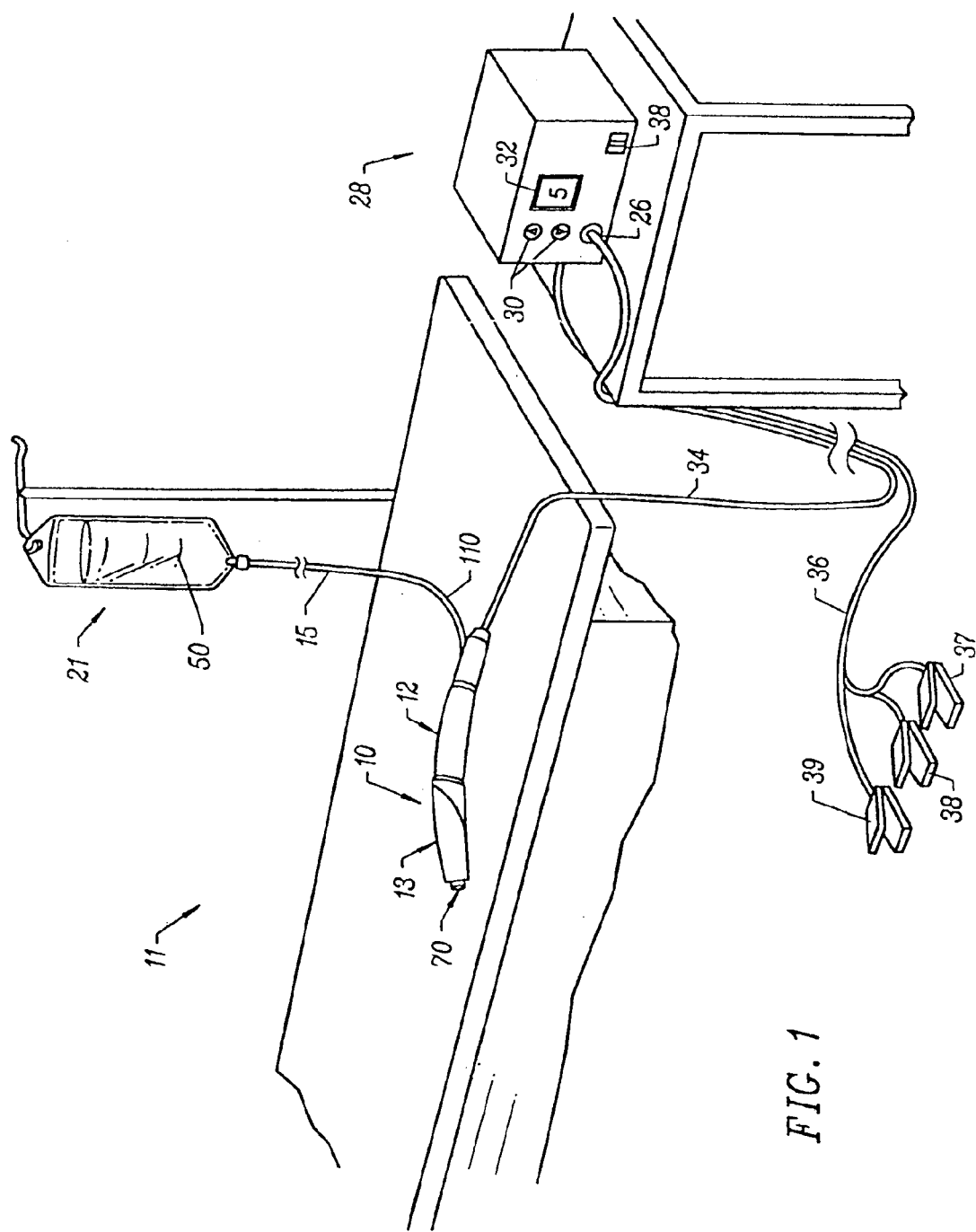
FIG. 1 is a perspective view of an electrosurgical system for treating a patient's skin including an electrosurgical generator and an electrosurgical probe or handpiece.

The present invention provides systems and methods for selectively applying electrical energy to a target location within or on a patient's body, particularly including procedures on an external body surface, such as epidermal and dermal tissues in the skin, or the underlying cutaneous tissue. For convenience, the remaining disclosure will be directed specifically to skin tissue cutting, ablation, incising or removal in the epidermis or dermis, e.g., the removal of pigmentations, vascular lesions (e.g., leg veins), scars, tattoos, etc., and for other surgical procedures on the skin, such as tissue rejuvenation, blepharoplasty, browlifts, liposuction, cosmetic surgery, wrinkle removal, hair removal and/or transplant procedures. However, it will be appreciated that the system and method can be applied equally well to procedures involving other tissues of the body, as well as to other procedures including open surgery, arthroscopic surgery, laparoscopic surgery, thoracoscopic surgery, and other endoscopic surgical procedures.

The present invention applies high frequency (RF) electrical energy to one or more electrode terminals adjacent an external body surface, such as the outer surface of the skin, to remove and/or modify the structure of tissue structures within the skin. Depending on the specific cosmetic procedure, the present invention may be used to: (1) volumetrically remove tissue or hair (i.e., ablate or effect molecular dissociation of the tissue structure); (2) decouple or separate a tissue layer from an underlying tissue layer so that the tissue layer can later be removed; (3) shrink or contract collagen connective tissue; (4) create precise incisions in the external skin surface; and/or (5) coagulate blood vessels underlying the surface of the skin.

In one method of the present invention, incisions are created in the skin by volumetrically removing or ablating tissue along a cutting path. In this procedure, a high frequency voltage difference is applied between one or more electrode terminal(s) and one or more return electrode(s) to develop high electric field intensities in the vicinity of the target tissue site. The high electric field intensities lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the electrode terminal(s) in the region between the distal tip of the electrode terminal(s) and the target tissue. The electrically conductive fluid may be a liquid, such as isotonic saline, delivered to the target site, or a viscous fluid, such as a gel, that is located at the target site. In the latter embodiment, the electrode terminal(s) are submersed in the electrically conductive gel during the surgical procedure. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. This energy may be in the form of energetic photons (e.g., ultraviolet radiation), energetic particles (e.g., electrons) or a combination thereof. A more detailed description of this phenomena can be found in commonly assigned U.S. Pat. No. 5,683,366 the complete disclosure of which is incorporated herein by reference.

In the above procedure, it may also be desirable to effect collagen shrinkage or contraction of the tissue layers underlying the removed or ablated epidermal tissue. In these procedures, the temperature of the electrode terminal(s) can be carefully controlled such that sufficient thermal energy is transferred to these underlying layers to contract the collagen connective tissue. The thermal energy may be transferred directly through RF current that passes through and resistively heats the underlying tissue layers, or it may be transferred indirectly by heating the electrically conducting fluid, and allowing the heated fluid to contact the underlying layers after the epidermal layers have been removed. A complete description of suitable methods of contracting collagen tissue with RF energy is described in U.S. patent application Ser. No. 08/942,580, filed on Oct. 2, 1997, the complete disclosure of which has previously been incorporated herein by reference.

In other procedures, it may be desired to treat vascular lesions, such as port wine stains, face veins, telangiectasis, birth marks, varicose veins and the like. In these procedures, electrical energy is applied to the vessel such that the energy is absorbed in the blood, which coagulates and collapses the vessel. The blood vessel may be accessed in a variety of manners. For example, high frequency voltage may be applied to one or more electrode terminals at the surface of the skin such that sufficient thermal energy is delivered through the skin to the blood vessel to coagulate the blood therein. Alternatively, the skin may be pierced with the sharpened tip of a probe. In this method, the probe is advanced to a location adjacent to the vessel to be treated, and high frequency energy is applied to the distal end of the probe to coagulate and collapse the vessel at that location. This procedure may be repeated at multiple sites along the length of the vessel so that it will collapse along its length.

In other methods, the high frequency voltage may be focused onto a small spot on the surface of the skin over the vessel to be treated such that a small volume (e.g., channel or hole) of skin is ablated until the vessel is reached. Systems and methods for forming channels or holes through tissue with electrical energy are provided in U.S. Pat. No. 5,683,366.

In one method of the present invention, one or more electrode terminals are brought into close proximity to tissue at a target site, and the power supply is activated in the ablation mode such that sufficient voltage is applied between the electrode terminals and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the electrode terminals may be pressed against the severed vessel to provide sealing and/or coagulation of the vessel. Alternatively, a coagulation electrode located on the same or a different instrument may be pressed against the severed vessel. Once the vessel is adequately sealed, the surgeon activates a control (e.g., another foot pedal) to increase the voltage of the power supply back into the ablation mode.

The present invention is also useful for cutting or incising tissue around nerves, such as cranial nerves, e.g., facial nerves, vestibulocochlear nerves and the like. One of the significant drawbacks with the prior art RF devices and lasers is that these devices do not differentiate between the target tissue and the surrounding nerves or bone. Therefore, the surgeon must be extremely careful during these procedures to avoid damage to the nerves within and around the target site. In the present invention, the Coblation™ process for removing tissue results in extremely small depths of collateral tissue damage as discussed above. This allows the surgeon to remove or cut tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Nerves usually comprise a connective tissue sheath, or epineurium, enclosing the bundles of nerve fibers, each bundle being surrounded by its own sheath of connective tissue (the perineurium) to protect these nerve fibers. The outer protective tissue sheath or epineurium typically comprises a fatty tissue (e.g., adipose tissue) having substantially different electrical properties than the normal target tissue, such as the turbinates, polyps, mucus tissue or the like, that are, for example, removed from the nose during sinus procedures. The system of the present invention measures the electrical properties of the tissue at the tip of the probe with one or more electrode terminal(s). These electrical properties may include electrical conductivity at one, several or a range of frequencies (e.g., in the range from 1 kHz to 100 MHz), dielectric constant, capacitance or combinations of these. In this embodiment, an audible signal may be produced when the sensing electrode (s) at the tip of the probe detects the fatty tissue surrounding a nerve, or direct feedback control can be provided to only supply power to the electrode terminal(s) either individually or to the complete array of electrodes, if and when the tissue encountered at the tip or working end of the probe is normal tissue based on the measured electrical properties.

In addition to the above, applicant has discovered that the Coblation™ mechanism of the present invention can be manipulated to ablate or cut certain tissue structures, while having little effect on other tissue structures. As discussed above, the present invention uses a technique of vaporizing electrically conductive fluid to form a plasma layer or pocket around the electrode terminal(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conducting liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of electrode terminals; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose) tissue has double bonds that require a substantially higher energy level than 4 to 5 eV to break. Accordingly, the present invention in its current configuration generally does not ablate or remove such fatty tissue. Of course, factors may be changed such that these double bonds can also be broken in a similar fashion as the single bonds (e.g., increasing voltage or changing the electrode configuration to increase the current density at the electrode tips). A more complete description of this phenomena can be found in co-pending U.S. patent application Ser. No. 09/032,375, filed Feb. 27, 1998 the complete disclosure of which is incorporated herein by reference.

The present invention also provides systems, apparatus and methods for selectively removing tumors, e.g., facial tumors, or other undesirable body structures while minimizing the spread of viable cells from the tumor. Conventional techniques for removing such tumors generally result in the production of smoke in the surgical setting, termed an electrosurgical or laser plume, which can spread intact, viable bacterial or viral particles from the tumor or lesion to the surgical team or to other portions of the patient's body. This potential spread of viable cells or particles has resulted in increased concerns over the proliferation of certain debilitating and fatal diseases, such as hepatitis, herpes, HIV and papillomavirus. In the present invention, high frequency voltage is applied between the electrode terminal(s) and one or more return electrode(s) to volumetrically remove at least a portion of the tissue cells in the tumor through the dissociation or disintegration of organic molecules into non-viable atoms and molecules. Specifically, the present invention converts the solid tissue cells into non-condensable gases that are no longer intact or viable, and thus, not capable of spreading viable tumor particles to other portions of the patient's brain or to the surgical staff. The high frequency voltage is preferably selected to effect controlled removal of these tissue cells while minimizing substantial tissue necrosis to surrounding or underlying tissue. A more complete description of this phenomena can be found in co-pending U.S. patent application Ser. No. 09/109, 219, filed Jun. 30, 1998, the complete disclosure of which is incorporated herein by reference.

The electrosurgical probe will comprise a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. For dermatology procedures, the shaft will have any suitable length and diameter that would facilitate handling by the surgeon.

The present invention may use a single active electrode terminal or an electrode array distributed over a contact surface of a probe. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive liquids, such as blood, normal saline, electrically conductive gel and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the probe to form a single wire that couples to a power source.

The electrode terminal(s) are preferably supported within or by an inorganic insulating support positioned near the distal end of the instrument shaft. The return electrode may be located on the instrument shaft, on another instrument or on the external surface of the patient (i.e., a dispersive pad). The close proximity of nerves and other sensitive tissue in the face, however, makes a bipolar design more preferable because this minimizes the current flow through facial tissue and surrounding nerves. Accordingly, the return electrode is preferably either integrated with the instrument body, or another instrument located in close proximity to the distal end of the instrument. The proximal end of the instrument will include the appropriate electrical connections for coupling the return electrode(s) and the electrode terminal(s) to a high frequency power supply, such as an electrosurgical generator.

The current flow path between the electrode terminals and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conducting fluid between the active and return electrodes is described in U.S. Pat. No. 5,697,281, previously incorporated herein by reference. Alternatively, the body's natural conductive fluids, such as blood, may be sufficient to establish a conductive path between the return electrode(s) and the electrode terminal(s), and to provide the conditions for establishing a vapor layer, as described above. However, conductive fluid that is introduced to the patient is generally preferred over blood because blood will tend to coagulate at certain temperatures. Advantageously, a liquid electrically conductive fluid (e.g., isotonic saline) may be used to concurrently "bathe" the target tissue surface to provide an additional means for removing any tissue, and to cool the region of the target tissue ablated in the previous moment.

The power supply may include a fluid interlock for interrupting power to the electrode terminal(s) when there is insufficient conductive fluid around the electrode terminal (s). This ensures that the instrument will not be activated when conductive fluid is not present, minimizing the tissue damage that may otherwise occur. A more complete description of such a fluid interlock can be found in commonly assigned, co-pending U.S. application Ser. No. 09/058,336, filed Apr. 10, 1998, the complete disclosure of which is incorporated herein by reference.

In some procedures, it may also be necessary to retrieve or aspirate the electrically conductive fluid, the non-condensable gaseous products of ablation and/or fatty tissue fragments that have not been completed ablated in situ. For example, in blepharoplasty procedures, it may be desired to remove the underlying fatty tissue from the patient's eyelids with the present invention. This may be accomplished by first breaking down this tissue with the Coblation mechanism of the present invention, and then aspirated the remaining tissue fragments from the patient. Accordingly, the system of the present invention may include one or more suction lumen(s) in the instrument, or on another instrument, coupled to a suitable vacuum source for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation electrode terminal(s), or the same electrode(s) may serve both functions. A more complete description of instruments incorporating aspiration electrode(s) can be found in commonly assigned, co-pending patent application entitled "Systems And Methods For Tissue Resection, Ablation And Aspiration", filed Jan. 21, 1998, the complete disclosure of which is incorporated herein by reference.

In one configuration, each individual electrode terminal in the electrode array is electrically insulated from all other electrode terminals in the array within said probe and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the probe, connectors, cable, controller or along the conductive path from the controller to the distal tip of the probe.

Alternatively, the resistance and/or capacitance may occur on the surface of the active electrode terminal(s) due to oxide layers which form selected electrode terminals (e.g., titanium or a resistive coating on the surface of metal, such as platinum).

The tip region of the probe may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode may be a tubular member of conductive material proximal to the electrode array at the tip which also serves as a conduit for the supply of the electrically conducting fluid between the active and return electrodes. The application of high frequency voltage between the return electrode and the electrode array results in the generation of high electric field intensities at the distal tips of the electrode terminals with conduction of high frequency current from each individual electrode terminal to the return electrode. The current flow from each individual electrode terminal to the return electrode is controlled by either active or passive means, or a combination thereof, to deliver electrical energy to the surrounding conductive fluid while minimizing energy delivery to surrounding (non-target) tissue.

The application of a high frequency voltage between the return electrode and the electrode array for appropriate time intervals effects heating of the conductive fluid and contraction of the target tissue. The tissue volume over which energy is dissipated (i.e., a high current density exists) may be precisely controlled, for example, by the use of a multiplicity of small electrode terminals whose effective diameters or principal dimensions range from about 10 mm to 0.01 mm, preferably from about 5 mm to 0.05 mm, and more preferably from about 3 mm to 0.1 mm. Electrode areas for both circular and non-circular terminals will have a contact area (per electrode terminal) below 25 $mm^2$, preferably being in the range from 0.0001 $mm^2$ to 1 $mm^2$, and more preferably from 0.005 $mm^2$ to 0.5 $mm^2$. The circumscribed area of the electrode array is in the range from 0.25 $mm^2$ to 75 $mm^2$, preferably from 0.5 $mm^2$ to 40 $mm^2$, and will usually include at least two isolated electrode terminals and preferably about three electrode terminals. Of course, the array may include more than three electrode terminals (e.g., 50 or more electrode terminals) disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The electrode terminal(s) are formed over a tissue treatment surface on the shaft of the electrosurgical probe. The return electrode surface will be recessed relative to the distal end of the probe and may be recessed within a fluid conduit provided for the introduction of electrically conducting fluid to the site of the target tissue and electrode terminal(s).

The area of the tissue treatment surface can vary widely, and the tissue treatment surface can assume a variety of geometries, with particular areas and geometries being selected for specific applications. Active electrode surfaces can have areas in the range from 0.25 $mm^2$ to 75 $mm^2$, usually being from about 0.5 $mm^2$ to 40 $mm^2$. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical probe shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical probe shaft (e.g., in the manner of a spatula), facilitating access to certain body structures in endoscopic procedures.

In the representative embodiment, the electrode array comprises a plurality of substantially elongate electrode terminals spaced on the contact surface of the shaft. Preferably, the contact surface is an electrically insulating electrode support member extending from the shaft of the probe. The elongate electrode terminals will typically have a length of about 0.5 to 30 mm, preferably about 1 to 15 mm and more preferably about 3 to 7 mm. The width of the elongate electrode terminals is usually about 0.01 to 2 mm, preferably about 0.05 to 1 mm, and more preferably about 0.1 to 0.5 mm. The elongate electrode terminals will be spaced from each other by a distance of about 0.05 to 4 mm, preferably about 0.1 mm to 2 mm. Although the array may comprise one electrode terminal or over 50 electrode terminals, applicant has found that two to ten electrode terminals provides a substantially uniform application of energy to the tissue at the treatment site.

In the exemplary embodiment, the electrode support comprises a plurality of wafer layers bonded together, e.g., by a glass adhesive or the like. The wafer layers each have conductive strips printed thereon to form the electrode terminal(s) and the return electrode(s). In one embodiment, the proximal end of the wafer layers will have a number of holes extending from the conductor strips to an exposed surface of the wafer layers for connection to electrical conductor lead traces in the electrosurgical probe or handpiece. The wafer layers preferably comprise a ceramic material, such as alumina, and the electrode will preferably comprise a metallic material, such as gold, platinum, palladium, tungsten, silver or the like. Suitable multilayer ceramic electrodes are commercially available from e.g., VisPro Corporation of Beaverton, Oreg.

The electrically conducting fluid should have a threshold conductivity to provide a suitable conductive path between the return electrode and the electrode terminal(s). The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm. Alternatively, the fluid may be an electrically conductive gel or spray, such as a saline electrolyte gel, a conductive ECG spray, an electrode conductivity gel, an ultrasound transmission or scanning gel, or the like. Suitable gels or sprays are commercially available from Graham-Field, Inc. of Hauppauge, N.Y.

In some embodiments, the electrode support and the fluid outlet may be recessed from an outer surface of the probe or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor or plasma layer between the electrode terminal(s) and the tissue at the treatment site throughout the procedure, which reduces the thermal damage that might otherwise occur if the vapor layer were extinguished due to a lack of conductive fluid. The electrically conductive fluid also helps maintain the tissue temperature as low as possible during the procedure.

The voltage applied between the return electrode and the electrode array will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the electrode terminal size, the operating frequency and the operation mode of the particular procedure or desired effect on the tissue (i.e., contraction, coagulation or ablation). Typically, the peak-to-peak voltage will be in the range of 10 to 2000 volts and preferably in the range of 20 to 1200 volts and more preferably in the range of about 40 to 800 volts (again, depending on the electrode size, the operating frequency and the operation mode).

Figure 21:
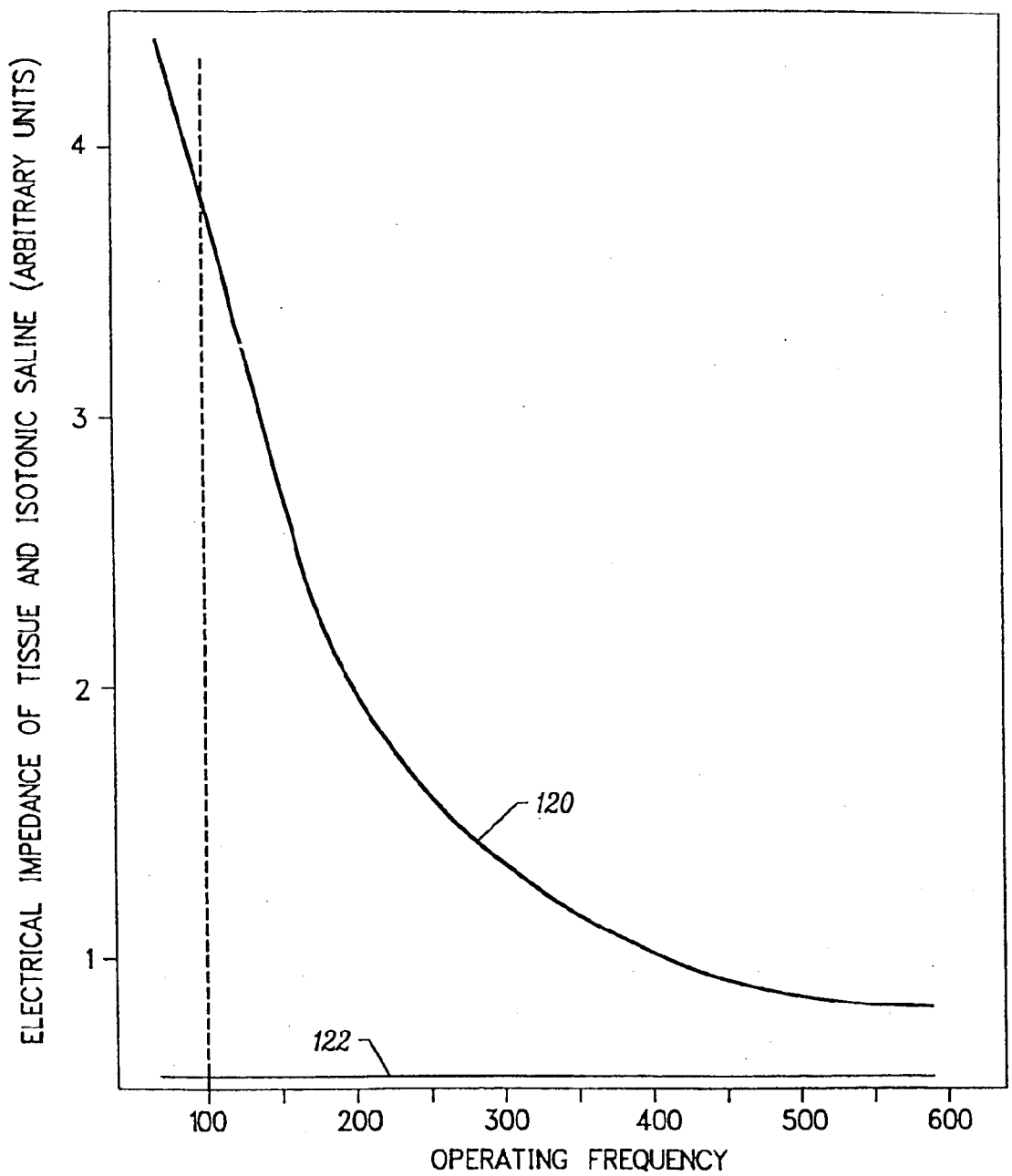
FIG. 21 is a graph illustrating the electrical impedance of tissue and isotonic saline with operating frequency.

An important aspect of the present invention is the discovery that the frequency of the output voltage of the generator can be selected to control the depth of tissue heating. Referring to FIG. 21, the electrical impedance of tissue is known to decrease with increasing frequency due to the electrical properties of cell membranes which surround electrically conductive cellular fluid. As shown, the electrical impedance of tissue to current at a frequency of 100 kHz is on the order of four times larger than at a frequency of 450 to 500 kHz. As a result of the higher tissue impedance, the current flux lines tend to penetrate less deeply resulting in a smaller depth of tissue heating. This principle of operation of the present invention can be used to advantage in applications where the depth of tissue heating is to be maintained small (e.g., 0.2 to 0.5 mm). Preferably, the operating frequency should be below 350 kHz for applications requiring shallow depths of tissue heating (e.g., less than 1.5 mm). Conversely, in situations where much larger depths of tissue heating are to be effected, a higher output voltage frequency may be used. By way of example, to achieve therapeutic collagen shrinkage to a depth of 1.5 to 3.0 mm, a higher operating frequency may be used (e.g., 500 kHz). Alternatively, the diameter of the electrode terminals and/or the spacing between the outer perimeter of the electrode terminals and the electrode support member may be selected to increase the depth of current penetration. By way of example, increasing the distance between the outer perimeter of the support member and the electrode terminals will increase the depth of heating for a given operating frequency.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.001%.

The preferred power source of the present invention delivers a high frequency current selectable to generate average power levels ranging from several milliwatts to tens of watts per electrode, depending on the volume of target tissue being heated, the total number of electrode(s) and/or the maximum allowed temperature selected for the probe tip. The power source allows the user to select the voltage level according to the specific requirements of a particular arthroscopic surgery, cosmetic surgery, dermatological procedure, ophthalmic procedures, open surgery or other endoscopic surgery procedure. A description of a suitable power source can be found in U.S. Provisional Patent Application No. 60/062,997, filed on Oct. 23, 1997, the complete disclosure of which has been previously incorporated herein by reference.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the size of the electrode terminal(s), the desired tissue heating rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel).

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source.

During the surgical procedure, the distal end of the probe or the electrode terminal(s) may be maintained at a small distance away from the target tissue surface. This small spacing allows for the continual resupply of electrically conducting fluid into the interface between the electrode terminal(s) and the target tissue surface. This continual resupply of the electrically conducting fluid helps to ensure that the thin vapor layer will remain between electrode terminal(s) and the tissue surface. In addition, dynamic movement of the electrode terminal(s) over the tissue site allows the electrically conducting fluid to cool the tissue underlying and surrounding the target tissue to minimize thermal damage to this surrounding and underlying tissue. To that end, the electrically conducting fluid may be cooled to facilitate this cooling of the tissue. Typically, the active electrode(s) will be about 0.02 to 2 mm from the target tissue and preferably about 0.05 to 0.5 mm during the ablation process. One method of maintaining this space is to translate and/or rotate the probe transversely relative to the tissue, i.e., a light brushing motion, to maintain a thin vaporized layer or region between the active electrode and the tissue. Of course, if coagulation or collagen shrinkage of a deeper region of tissue is necessary (e.g., for sealing a bleeding vessel imbedded within the tissue), it may be desirable to press the electrode terminal(s) against the tissue to effect joulean heating therein.

Referring to FIG. 1, an electrosurgical system 11 generally comprises an electrosurgical handpiece or probe 10 connected to a power supply 28 for providing high frequency voltage to a target site and a fluid source 21 for supplying electrically conducting fluid 50 to probe 10. Probe 10 generally includes a proximal handle 12 and a distal tip 13 having an electrode support member 70 with one or an array of electrode terminals 58 and one or more return electrodes 100, 102 (see FIGS. 2, 4 and 5) disposed on the support member 70. A connecting cable 34 has a connector 26 for electrically coupling the electrodes in probe 10 to power supply 28. The electrode terminals 58 are electrically isolated from each other and each of the terminals 58 is connected to an active or passive control network within power supply 28 by means of a plurality of individually insulated conductors (not shown). A fluid supply tube 15 is connected to a fluid tube 110 of probe 10 for supplying electrically conducting fluid 50 to the distal tip 13 (see FIGS. 16 and 17).

Power supply 28 has an operator controllable voltage level adjustment 30 to change the applied voltage level, which is observable at a voltage level display 32. Power supply 28 also includes first, second and third foot pedals 37, 38, 39 and a cable 36 which is removably coupled to power supply 28. The foot pedals 37, 38, 39 allow the surgeon to remotely adjusting the energy level applied to electrode terminals 58. In an exemplary embodiment, first foot pedal 37 is used to place the power supply into the "ablation" mode and second foot pedal 38 places power supply 28 into the "coagulation" mode. The third foot pedal 39 allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing the vapor layer and accelerating these charged particles against the tissue). As discussed above, the requisite voltage level for ablation will vary depending on the number, size, shape and spacing of the electrodes, the distance in which the electrodes extend from the support member, etc. When the surgeon is using the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the coagulation mode, the power supply 28 applies a low enough voltage to one or more electrode terminals (or one or more coagulation electrodes) to avoid vaporization of the electrically conductive fluid, formation of a plasma and subsequent molecular dissociation of the tissue. The surgeon may automatically toggle the power supply between the ablation and coagulation modes by alternatively stepping on foot pedals 37, 38, respectively. This allows the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulate small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37. A specific design of a suitable power supply for use with the present invention can be found in U.S. Provisional Patent Application 60/062,997, filed Oct. 23, 1997.

Figure 2:
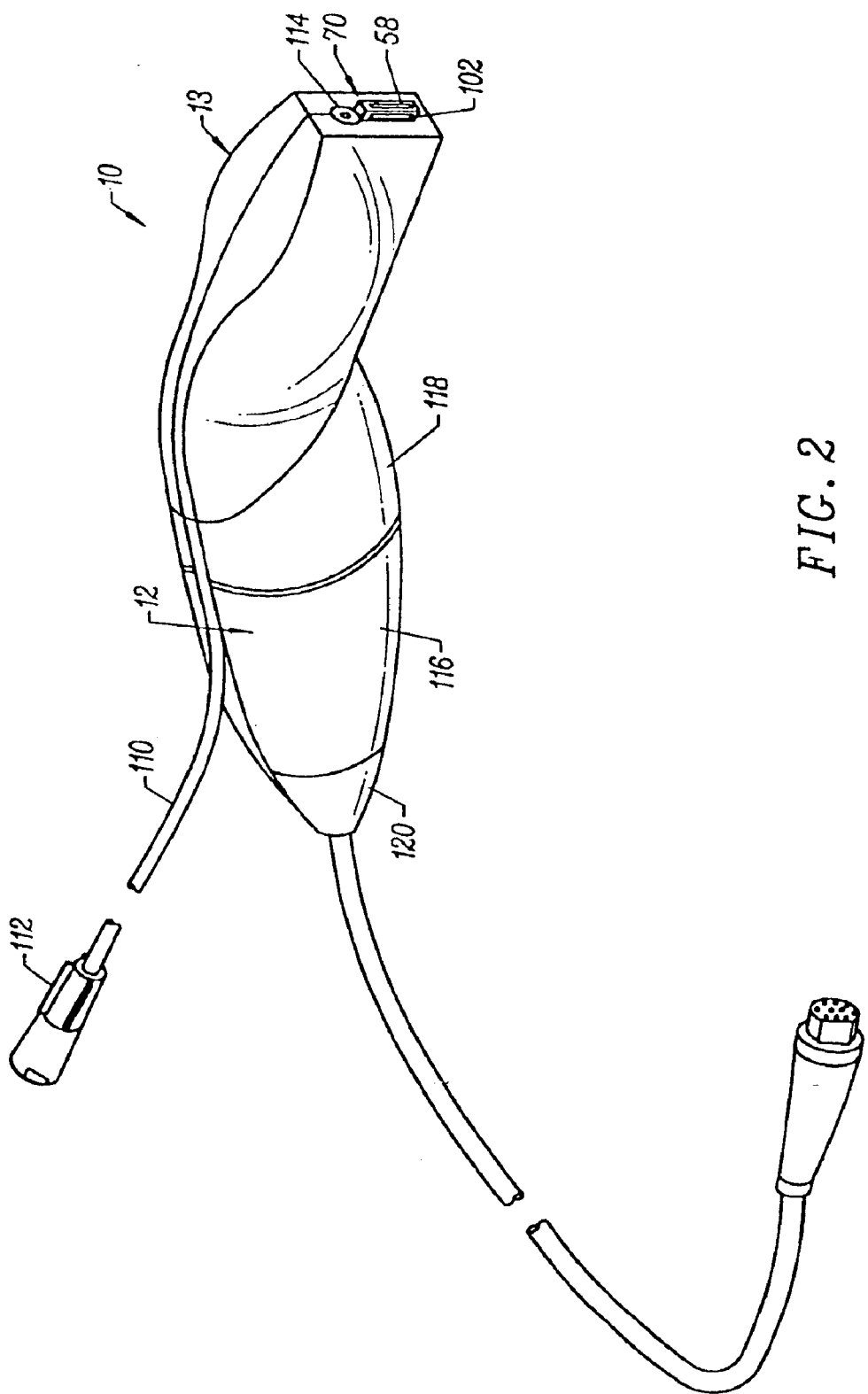
FIG. 2 is a perspective view of one embodiment of an electrosurgical probe constructed according to the principles of the present invention.
Figure 3A:
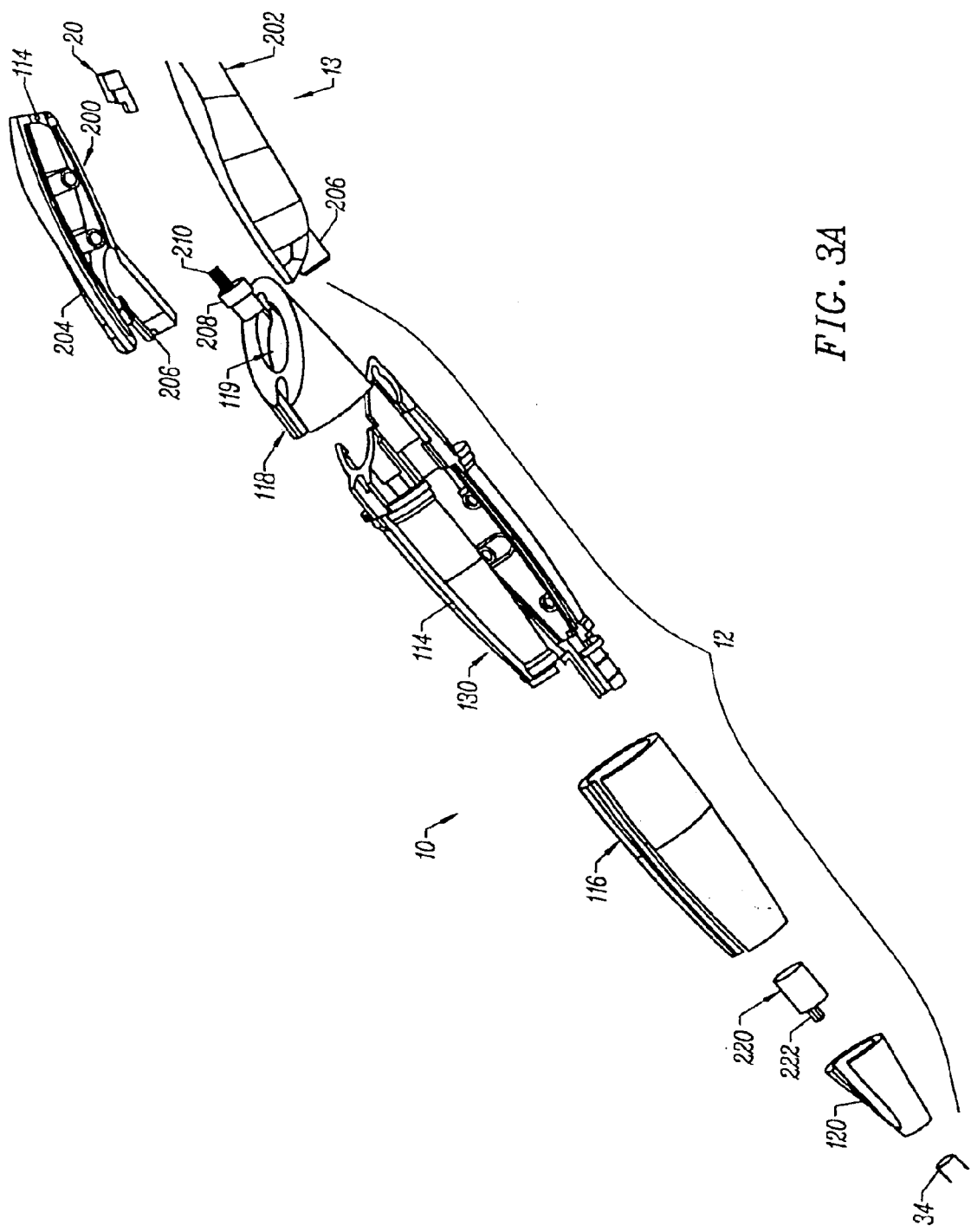
FIGS. 3A–3C are exploded, isometric views of the probe of FIG. 2.
Figure 3B:
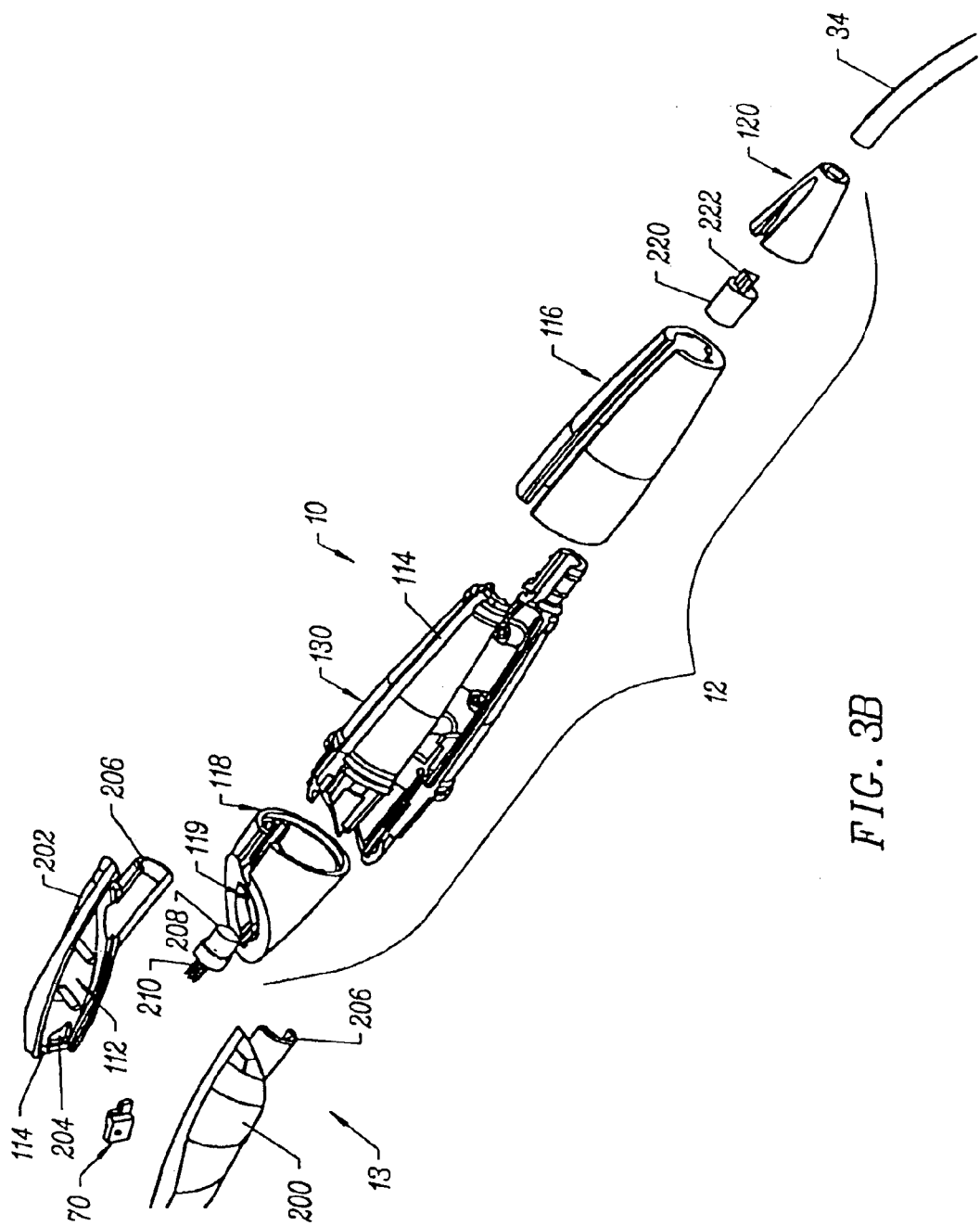
Figure 3C:
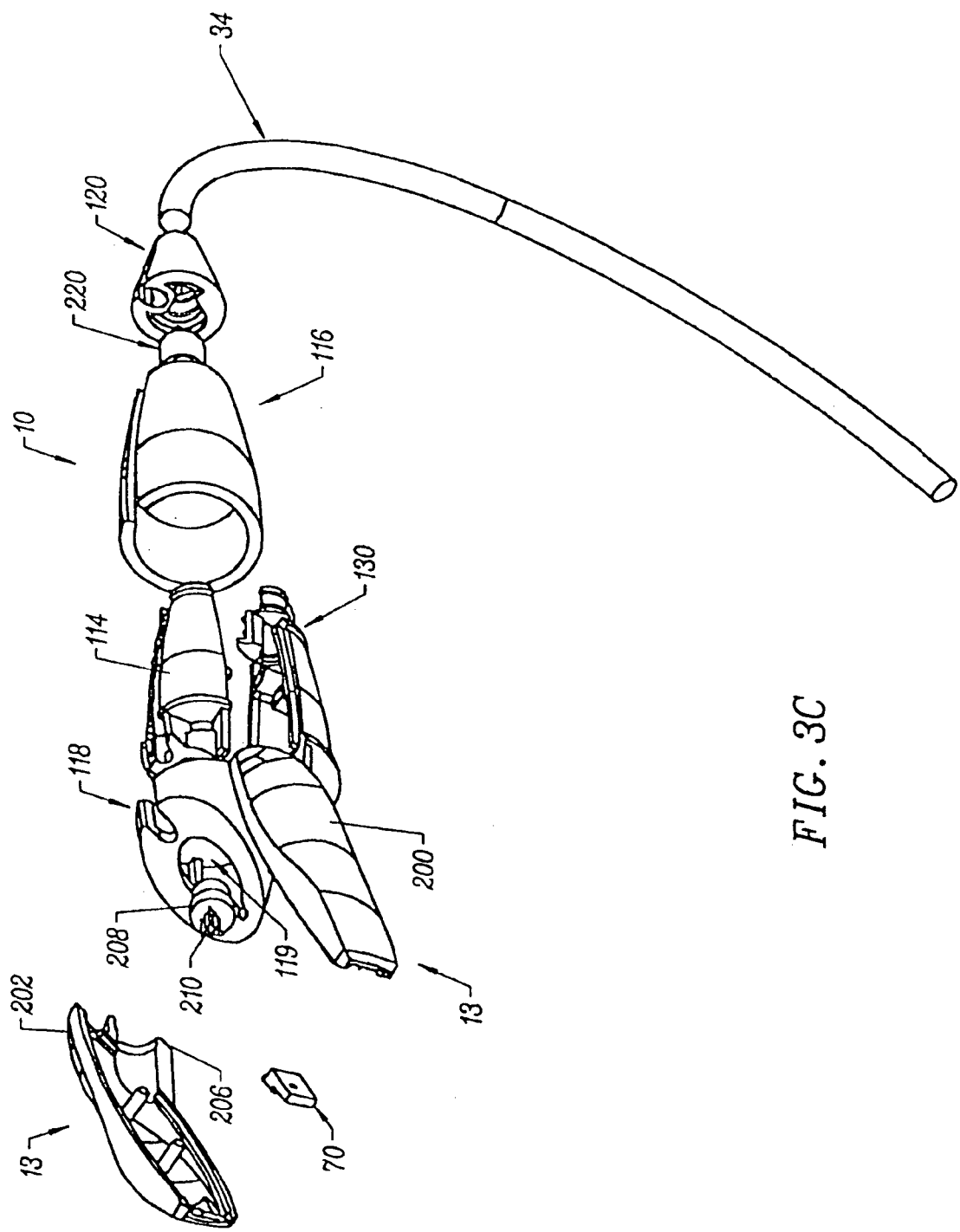
Figure 5:
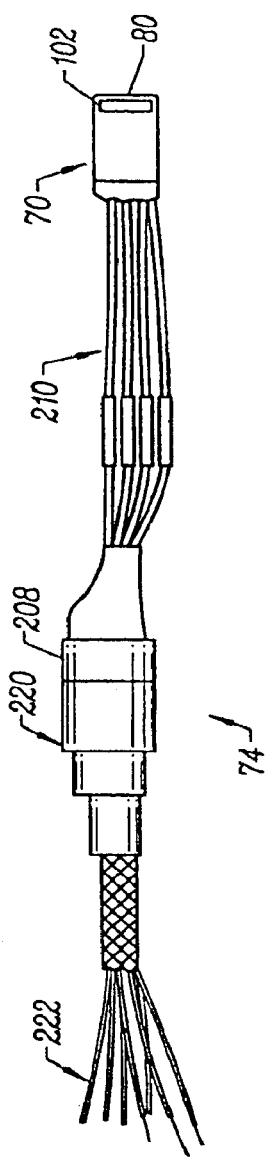
FIG. 5 illustrates the electrical connections and the electrode support of the handpiece in greater detail.

Referring now to FIGS. 2–5, an exemplary electrosurgical probe 10 comprises a shaft or disposable tip 13 removably coupled to a proximal handle 12, and an electrically insulating electrode support member 70 extending from tip 13 for supporting a plurality of electrode terminals 58 (see FIGS. 2 and 5). Tip 13 and handle 12 typically comprise a plastic material that is easily molded into a suitable shape for handling by the surgeon. As shown in FIGS. 3 and 5, handle 12 defines an inner cavity 72 that houses the electrical connections 74 (discussed below in reference to FIG. 5), and provides a suitable interface for connection to electrical connecting cable 34 (see FIG. 1). In the exemplary embodiment, handle 12 is constructed of a steam autoclavable plastic or metal (e.g., polyethylether keytone, or a stable metal alloy containing aluminum and/or zine, so that it can be re-used by sterilizing handle 12 between surgical procedures. High service temperature materials are preferred, such as a silicone cable jacket and a poly-ether-imide handpiece or ULTEM® that can withstand a repeated exposure to high temperatures.

Figure 4:
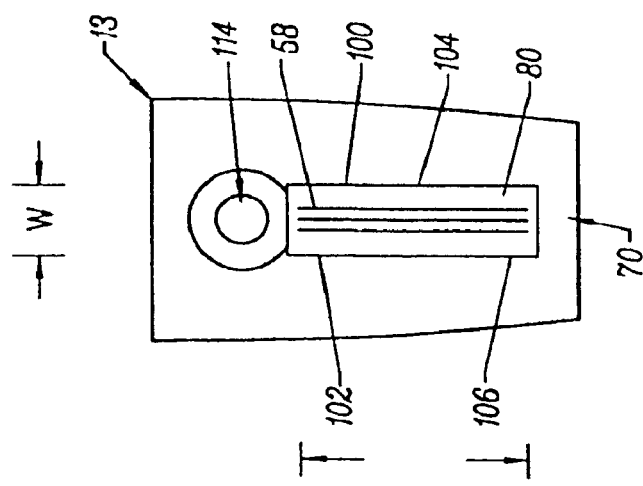
FIG. 4 is an end view of the distal tip of the probe, illustrating an electrode support with a plurality of electrode terminals.
Figure 6:
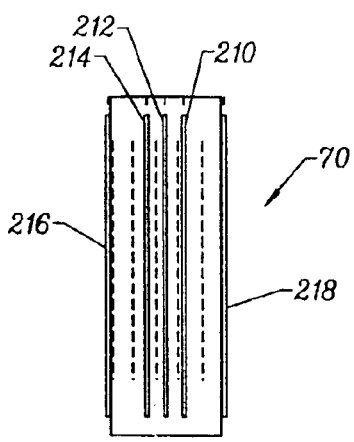
FIG. 6 is an end view of an exemplary electrode support comprising a multi-layer wafer with plated conductors for electrodes.
Figures 7, 8:
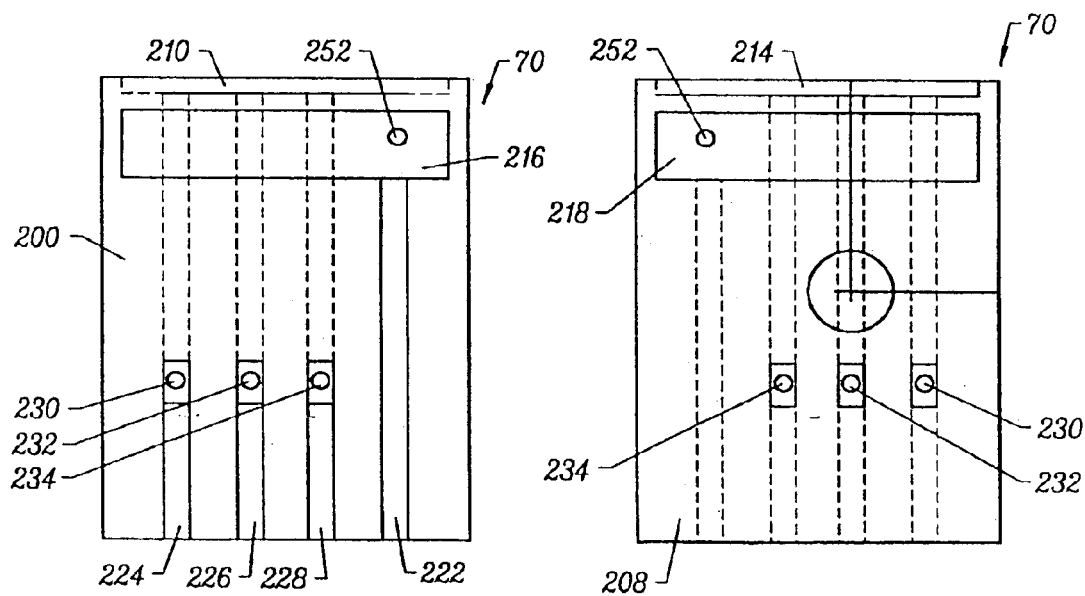
FIGS. 7 and 8 are side views of the electrode support of FIG. 7.

Referring to FIGS. 4A–4C, tip 13 preferably comprises first and second housing halves 200, 202 that snap fit together, and form a recess 204 therebetween for holding electrode support member 70 within the tip 13. Electrode support member 70 extends from the distal end of tip 13 (usually about 0.5 to 20 mm), and provides support for a plurality of electrically isolated electrode terminals 58 and one or more return electrode s 100, 102 (see FIG. 4). Alternatively, electrode support member 70 may be recessed from the distal end of tip 13 to help confine the electrically conductive fluid around the electrode terminals 58 during the surgical procedure, as discussed above. Electrode support member 70 has a substantially planar tissue treatment surface 80 that is usually disposed at an angle of about 10 to 90 degrees relative to the longitudinal axis of handle 12 to facilitate handling by the surgeon. In the exemplary embodiment, this function is accomplished by orienting tip 13 at an acute angle relative to the longitudinal axis of handle 12.

In the embodiment shown in FIGS. 2–5, probe 10 includes first and second return electrodes 100, 102 for completing the current path between electrode terminals 58 and power supply 28 (see FIG. 1). As shown, return electrodes 100, 102 preferably have fluid contact surfaces on either lateral surface 104, 106 of electrode support member 70 slightly proximal to tissue treatment surface 80, typically about 0.1 to 2 mm, preferably about 0.2 to 1 mm. Return electrodes 100, 102 will usually have an exposed surface area of about 5 mm2 to 25 mm2, preferably about 18 mm2 to about 20 mm2. Return electrodes 100, 102 are coupled to a connector 104 (details of this connection discussed below) that extends to the proximal end of handle 13, where it is suitably connected to power supply 28 (FIG. 1).

Referring to FIGS. 4A–4C and FIG. 5, tip 13 further includes a proximal hub 206 for supporting a male electrical connector 208 that holds a plurality of wires 210 each coupled to one of the electrode terminals 58 and the return electrodes 100, 102 on support member 70 (see FIGS. 7–13 for details of the representative support member 70). A female connector 220 housed within handle 12 is removably coupled to male connector 208, and a plurality of wires 222 extend from female connector 220 through a strain relief 224 to cable 34. Both sets of wires 210, 222 are insulated to prevent shorting in the event of fluid ingress into the probe 10. This design allows for removable connection of the electrodes in tip 13 with the connector 220 within handle 12 so that the handle can be re-used with different tips 13. Probe 10 will preferably also include an identification element, such as a coded resistor (not shown), for programming a particular voltage output range and mode of operation for the power supply. This allows the power supply to be employed with a variety of different probes for a variety of different applications.

As shown in FIG. 5, return electrodes 100, 102 are not directly connected to electrode terminals 58. To complete this current path so that electrode terminals 58 are electrically connected to return electrodes 102, 100, electrically conducting fluid (e.g., isotonic saline or electrically conducting gel) is located between the active and return electrodes during a surgical procedure. In the representative embodiment, probe 10 includes a fluid tube 110 (FIG. 2) for delivering electrically conductive fluid to the target site. Fluid tube 110 is sized to extend through a groove 114 in handle 13 and through an inner cavity 112 (FIG. 3 and FIGS. 4A–4C) in tip 12 to a distal opening 114 (FIG. 4) located adjacent electrode support member 70. Tube 110 extends all the way through inner cavity 112 to opening 114 to eliminate any possible fluid ingress into cavity 112. As shown in FIGS. 1 and 2, fluid tube 110 includes a proximal connector 112 for coupling to an electrically conductive fluid source 21.

Probe 10 will also include a valve or equivalent structure for controlling the flow rate of the electrically conducting fluid to the target site. In the representative embodiment shown in FIGS. 4A–4C, handle 12 comprises a main body 130 coupled between distal hub 118 and strain relief 120, and a rotatable sleeve 116 around main body 130. Distal hub 118 has an opening 119 for receiving proximal hub 206 of tip 13 for removably coupling the tip 13 to the handle 12. Sleeve 116 is rotatably coupled to strain relief 120 and distal hub 118 to provide a valve structure for fluid tube 110. As shown in FIG. 2, fluid tube 110 extends through groove 114 from strain relief 120, through main body 130 and distal hub 120 to tip 13. Rotation of sleeve 116 will impede, and eventually obstruct, the flow of fluid through tube 110. Of course, this fluid control may be provided by a variety of other input and valve devices, such as switches, buttons, etc.

In alternative embodiments, the fluid path may be directly formed in probe 10 by, for example, a central inner lumen or an annular gap (not shown) within the handle and the tip. This inner lumen may be formed near the perimeter of the probe 10 such that the electrically conducting fluid tends to flow radially inward towards the target site, or it may be formed towards the center of probe 10 so that the fluid flows radially outward. In addition, the electrically conducting fluid may be delivered from a fluid delivery element (not shown) that is separate from probe 10. In arthroscopic surgery, for example, the body cavity will be flooded with isotonic saline and the probe 10 will be introduced into this flooded cavity. Electrically conducting fluid will be continually resupplied to maintain the conduction path between return electrodes 100, 102 and electrode terminals 58. A more complete description of alternative electrosurgical probes incorporating one or more fluid lumen(s) can be found in U.S. Pat. No. 5,697,281, the complete disclosure of which has previously been incorporated herein by reference.

Referring to FIGS. 4 and 5, electrically isolated electrode terminals 58 are spaced apart over tissue treatment surface 80 of electrode support member 70. In the representative embodiment, the tissue treatment surface 80 has a rectangular cross-sectional shape with a length L in the range of about 0.5 mm to 20 mm (preferably about 2 to 10 mm) and a width W in the range from 0.3 mm to 10 mm (preferably about 0.5 to 4 mm). The individual electrode terminals 58 have the dimensions described above, and are preferably substantially flush with tissue treatment surface 80. Applicant has found that this configuration minimizes any sharp electrode edges and/or corners that would promote excessively high electric field intensities and associated current densities when a high frequency voltage is applied to the electrode terminals, thereby minimizing the rate of ablation as preferred for removing thin layers of tissue (e.g., epidermal layers).

It'should be noted that the electrode terminals 58 may protrude slightly outward from surface 80, typically by a distance from 0 mm to 2 mm, or the terminals may be recessed from this surface. For example, the electrode terminals 58 may be recessed by a distance from 0.01 mm to 1 mm, preferably 0.01 mm to 0.2 mm. In one embodiment of the invention, the electrode terminals are axially adjustable relative to the tissue treatment surface so that the surgeon can adjust the distance between the surface and the electrode terminals.

Referring now to FIGS. 7–13, an exemplary electrode support member 70 will be described in detail. As shown, electrode support member 70 preferably comprises a multilayer substrate comprising a suitable high temperature, electrically insulating material, such as ceramic. The multilayer substrate is a thin or thick-film hybrid having conductive strips that are adhered to the ceramic wafer layers (e.g., thick-film printed and fired onto or plated onto the ceramic wafers). The conductive strips typically comprise tungsten, gold, nickel, silver, platinum or equivalent materials. In the exemplary embodiment, the conductive strips comprise gold, and they are co-fired together with the wafer layers to form an integral package. The conductive strips are coupled to external wire connectors by holes or vias that are drilled through the ceramic layers, and plated or otherwise covered with conductive material.

In the representative embodiment, support member 70 comprises five ceramic layers 200, 202, 204, 206, 208 (see FIGS. 9–13), three gold plated electrode terminals 210, 212, 214 and first and second gold plated return electrodes 216, 218. As shown in FIGS. 8A, 9A and 9B, a first ceramic layer 200, which is one of the outer layers of support 70, includes first gold plated return electrode 216 on a lateral surface 220 thereof. First ceramic layer 200 further includes a gold conductive strip 222 extending from return electrode 216 to the proximal end of the layer 200 for coupling to a lead wire (not shown), and three gold conductive lines 224, 226, 228 extending from a mid-portion of the layer 200 to its proximal end. Conductive strips 224, 226, 228 are each coupled to one of the electrode terminals 210, 212, 214 by conductive holes or vias 230, 232, 234, respectively. As shown, all three vias 230, 232, 234 extend through wafer layer 200.

Figure 13:
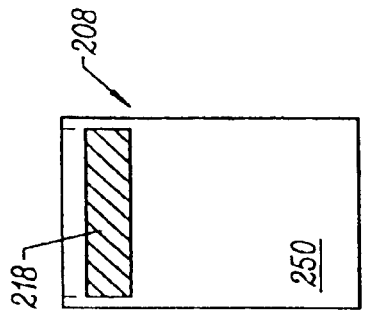
Figure 12A:
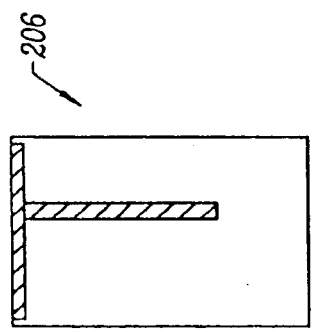
Figure 12B:
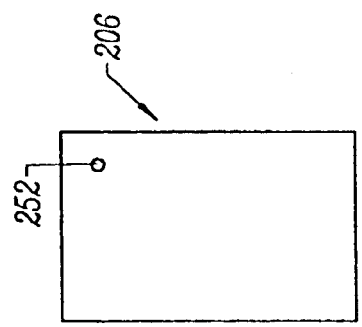
Figure 11A:
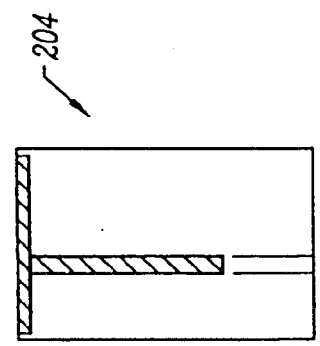
Figure 11B:
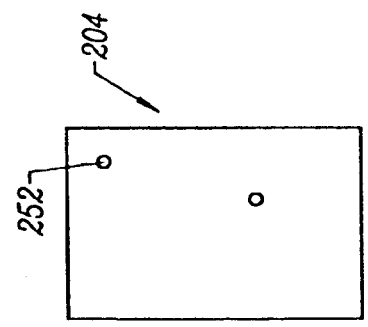

Referring to FIGS. 10A and 10B, a second wafer layer 202 is bonded between the outer wafer layer 200 and a middle wafer layer 204 (FIGS. 11A and 11B). As shown, first electrode terminal 210 is attached to the distal surface of second wafer layer 202, and a conductive strip 240 extends to via 230 to couple electrode terminal 210 to a lead wire. Similarly, wafer layers 204 and 206 (FIGS. 11 and 12) each have an electrode terminal 212, 214 plated to their distal surfaces, and a conductive strip 242, 244, respectively, extending to one of the vias 232, 234, respectively. Note that the vias only extend as far as necessary through the ceramic layers. As shown in FIG. 13, another outer wafer layer 208 has a second return electrode 218 plated to the lateral surface 250 of layer 208. The second return electrode 218 is coupled directly to the first return electrode 216 through a via 252 extending through the entire ceramic substrate.

Figure 14:
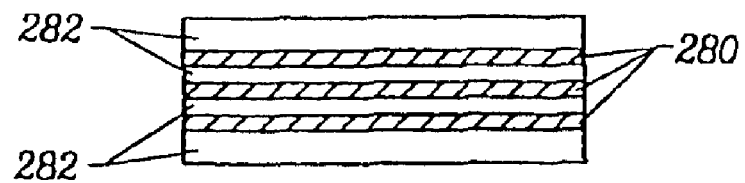
FIGS. 14 and 15 illustrate an alternative multi-layer wafer design according to the present invention.
Figure 15:
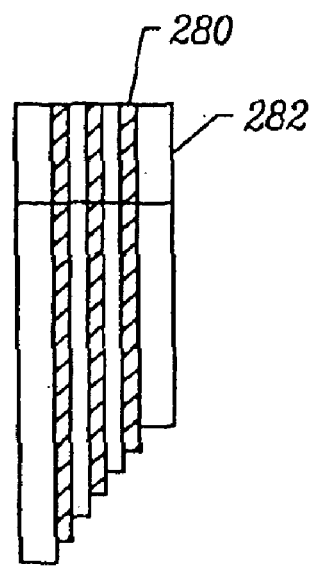

Of course, it will be recognized that a variety of different types of multilayer wafers may be constructed according to the present invention, For example, FIGS. 14 and 15 illustrate an alternative embodiment of the multilayer ceramic wafer, wherein the electrode terminals comprise planar strips 280 that are plated or otherwise bonded between the ceramic wafer layers 282 . Each of the planar strips 280 has a different length, as shown in FIG. 15, so that the electrode terminals can be electrically isolated from each other, and coupled to lead wires by vias (not shown).

Figure 16A:
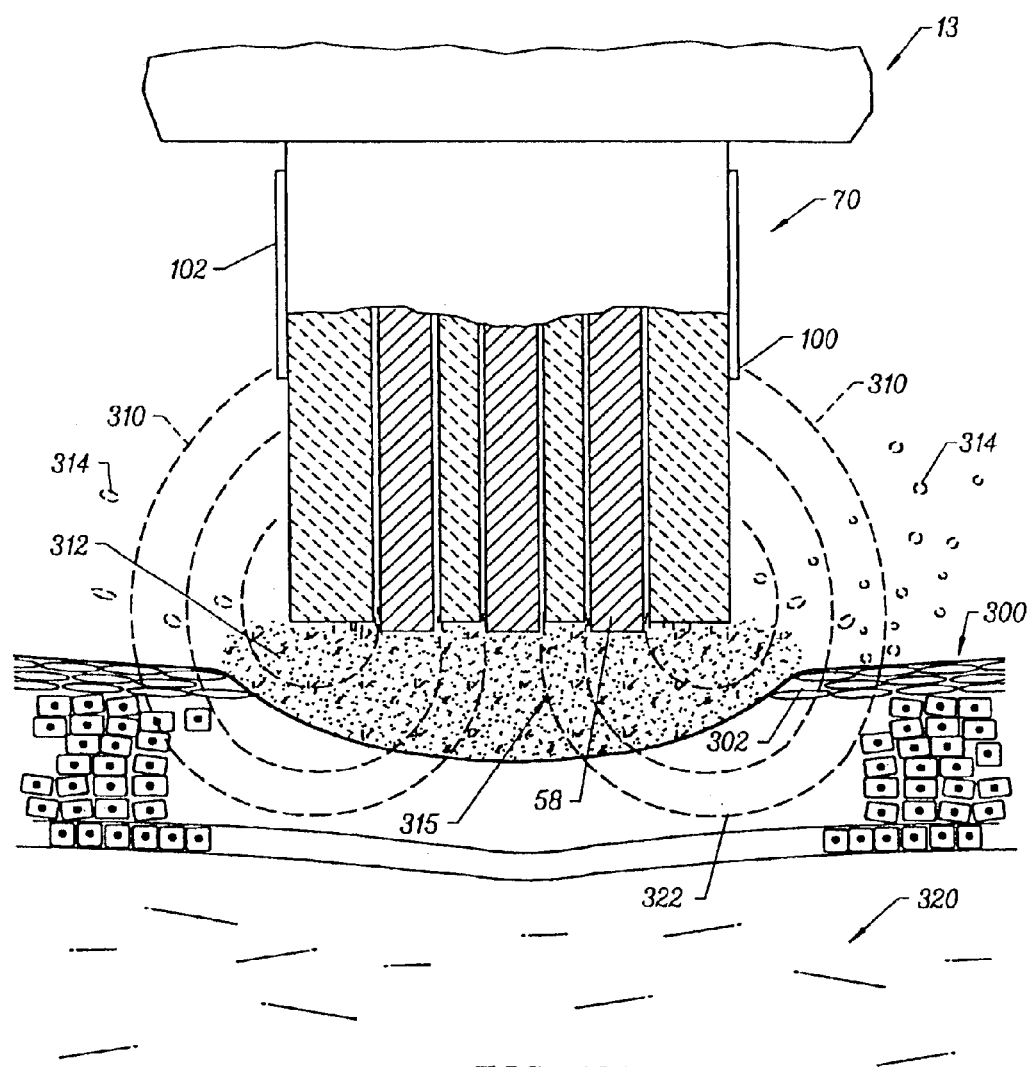
FIG. 16A illustrates a method for treating the outer layer of a patient's skin in a skin resurfacing procedure, wherein an outer layer of epidermis is removed or ablated and the collagen fibers in the underlying dermis are contracted.
Figure 16B:
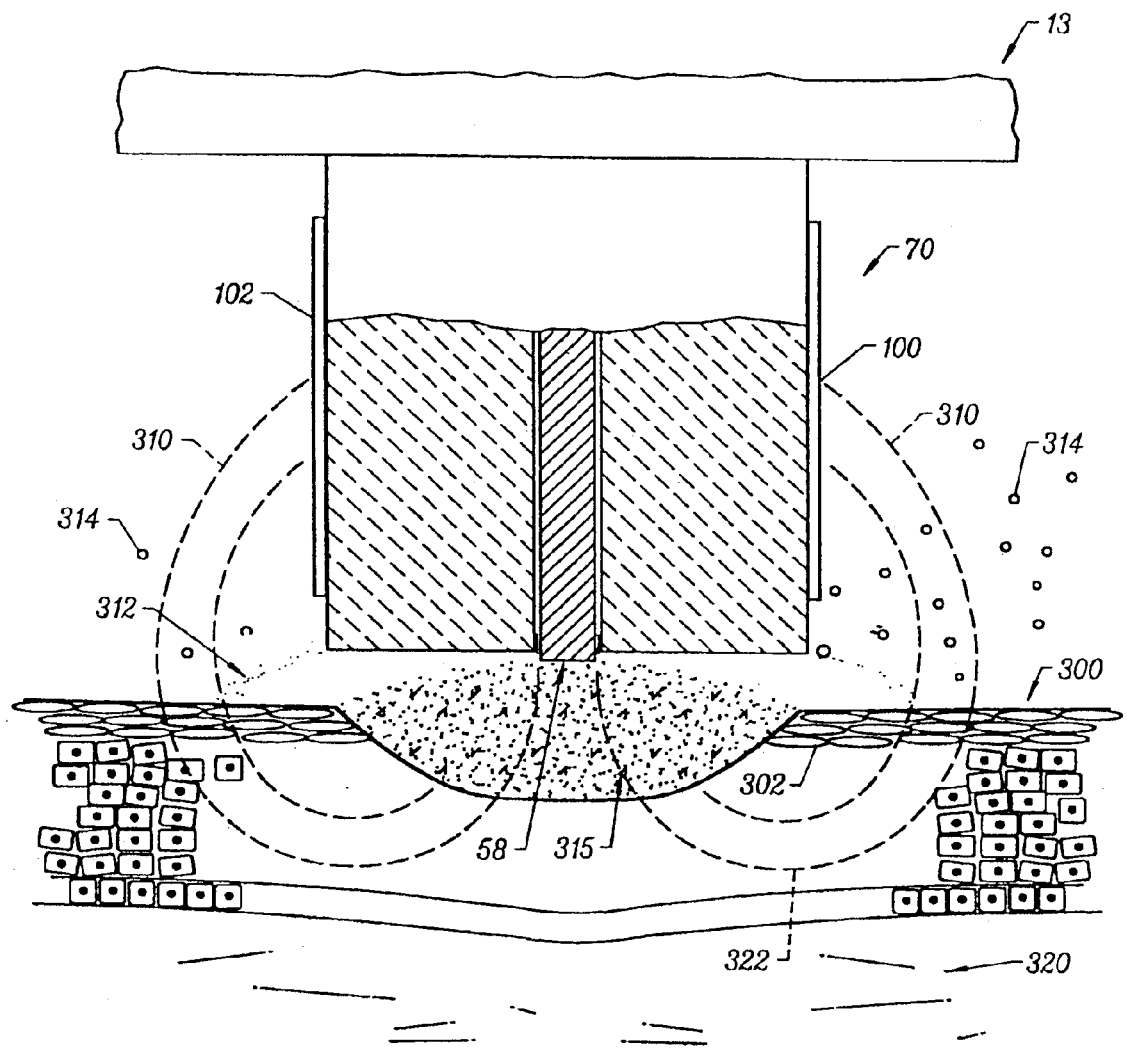
FIG. 16B illustrates a illustrates a method for treating the outer layer of a patient's skin in a skin resurfacing procedure with an electrosurgical probe having a single, active electrode terminal.

Referring now to FIGS. 16A and 16B, a method of treating tissue on the outer skin of a patient according to the present invention will now be described. As shown, distal tip 13 of probe 10 is positioned such that electrode support 70 is adjacent to the target tissue 302 at the treatment site 300. Electrically conducting fluid 304 is delivered through fluid tube 110 (FIG. 2) through distal hole 114 to the treatment site 300. The rate of fluid flow is controlled with rotatable sleeve 116 (FIG. 4A) such that the zone between the tissue 302 and electrode support 70 is constantly immersed in the fluid. The power supply 28 is then turned on and adjusted such that a high frequency voltage difference is applied between electrode terminal(s) 58 and return electrodes 100, 102. The electrically conductive fluid 304 provides the conduction path (see current flux lines 310) between electrode terminal (s) 58 and the return electrodes 100, 102 on either side of electrode support 70.

In the exemplary embodiment, the high frequency voltage is sufficient to convert the electrically conductive fluid 304 between the target tissue 302 and electrode terminals 58 into an ionized vapor layer 312 or plasma. As a result of the applied voltage difference between electrode terminals 58 and the target tissue 302 (i.e., the voltage gradient across the plasma layer 312), charged particles 315 in the plasma (viz., electrons) are accelerated towards the tissue. At sufficiently high voltage differences, these charged particles 315 gain sufficient energy to cause dissociation of the molecular bonds within tissue structures'. This molecular dissociation is accompanied by the volumetric removal (i.e., ablative sublimation) of tissue and the production of low molecular weight gases 314, such as oxygen, nitrogen, carbon dioxide, hydrogen and methane. The short range of the accelerated charged particles 315 within the target tissue 302 confines the molecular dissociation process to the surface layer to minimize damage and necrosis to the underlying tissue 320.

In some embodiments, the voltage difference will be sufficient enough to apply thermal energy to the underlying tissue 320. Preferably, this thermal energy will be sufficient to elevate the tissue temperature from normal body temperatures (e.g., 37° C.) to temperatures in the range of 45° C. to 90° C., preferably in the range from 55° C. to 70° C. and, for the case of skin, preferably in the range of about 55° C. to 62° C. This temperature elevation causes contraction of the collagen connective fibers within the underlying tissue 320. This method removes the surface layer of the skin, while tightening the underlying dermis to remove wrinkles and rejuvenate the skin.

Figure 17:
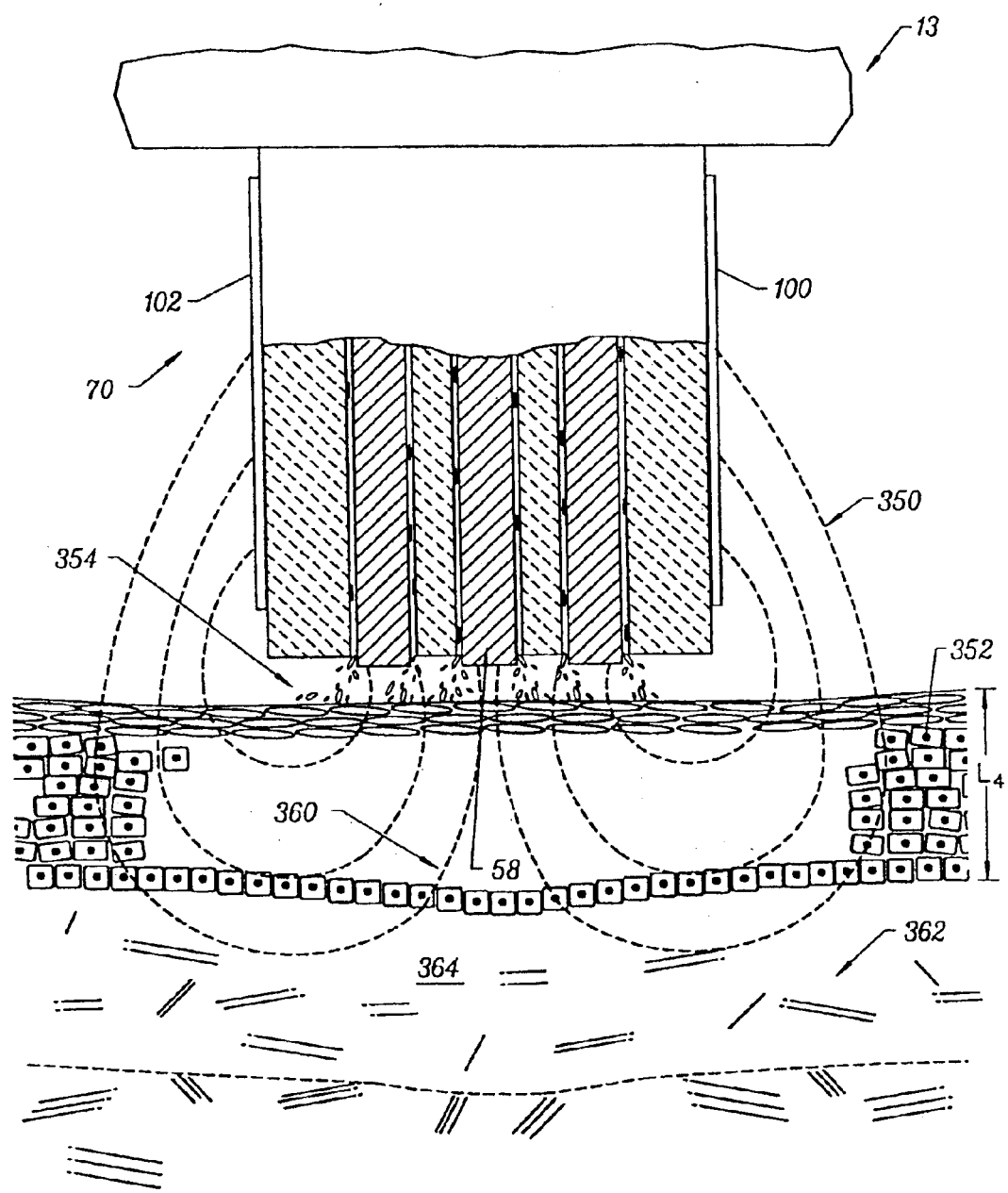
FIG. 17 illustrates a method of skin resurfacing wherein the epidermal layer is separated from the papillary dermis, and then removed by wiping away the separated layer.

An alternative method for skin rejuvenation or wrinkle removal is shown in FIG. 17. In this method, when a voltage difference is applied between the electrode terminals 58 and the return electrodes 100, 102, electrical current flows between the electrode terminals 58 and the return electrode 100, 102 along current flux lines 350. The current flux lines 350 flow a short distance, $L_4$ into the surface of epidermal tissue 352 and through the electrically conductive fluid 354 in the region above the surface of the tissue to complete the electrical path between the electrode terminals 58 and the return electrodes 100, 102. As a consequence of the electrical impedance of the tissue and the proper selection of the applied frequency, voltage and current, heating of the epidermal tissue 352 occurs in a region 360 below the surface of the tissue 352. This heating elevates the temperature of the tissue and separates the epidermal tissue layer 352 from the underlying papillary dermis 362. The epidermal tissue layer 352 may then be removed by flushing the treatment site, or by brushing away this tissue layer 352 with, for example, a cloth pad, gauze, etc. In skin rejuvenation procedures, collagen may be injected into the dermis after the epidermis has been removed to rejuvenate skin that has lost its elasticity.

In addition, the heating from current flux lines 350 may be sufficient to elevate the temperature of the tissue 364 in the papillary dermis 362 from normal body temperature (e.g. 37° C.) to a temperature in the range 55° C. to 85° C., preferably in the range from 60° C. to 70° C. This heating of the papillary dermis 362 will cause irreversible contraction of the collagen with the papillary dermis.

Figure 18A:
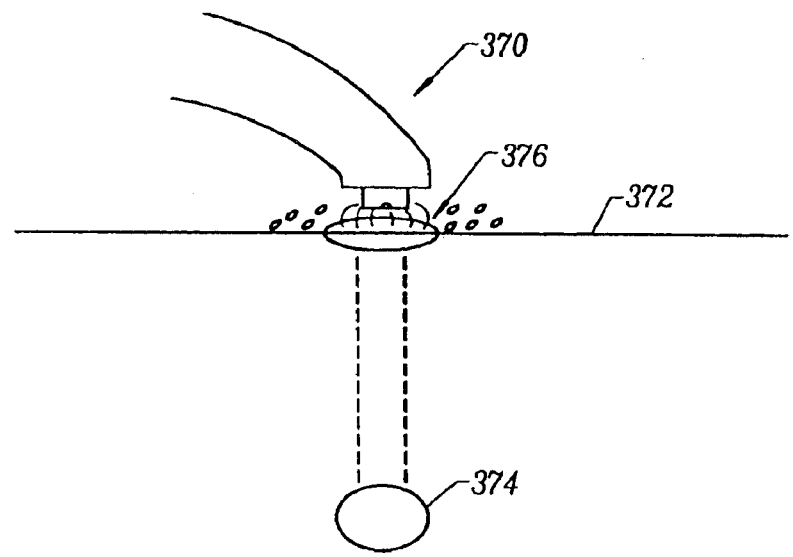
FIGS. 18A and 18B illustrate a method for treating a vascular lesion.
Figure 18B:
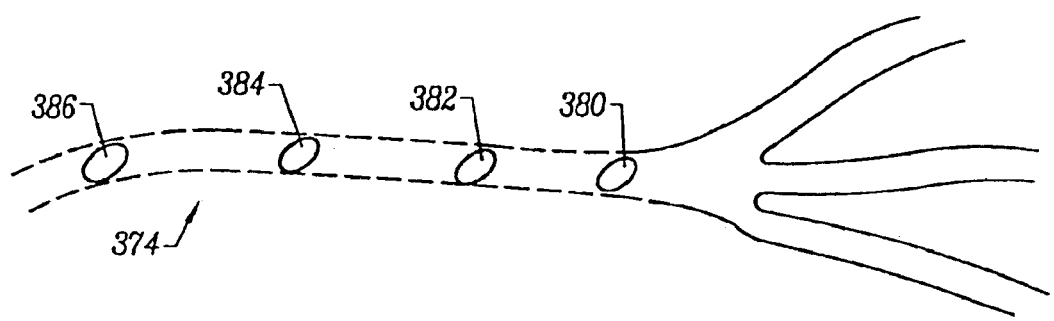

FIGS. 18A and 18B illustrate a method for treating a vascular lesion, such as a port wine stain, face vein, birth mark or the like. As shown in FIG. 18A, an electrosurgical probe 370 is placed on or adjacent to the surface of the skin 372 above the vessel 374 to be treated. A voltage difference is applied between the active and return electrodes (not shown) in the presence of electrically conductive fluid 376 to ablate or cause molecular dissociation of the tissue adjacent the probe 370. As the tissue is removed, the probe will be axially translated through the deepening hole to the vessel 374 (note that a substantially linear probe shaft is preferred in this embodiment). A more complete description of systems and methods for forming channels or holes through tissue is described in commonly assigned, U.S. Pat. No. 5,683,366, the complete disclosure of which is incorporated herein by reference. Once the probe approaches the vessel, thermal energy will be delivered into the vessel from the current flux lines as described above. This thermal energy will eventually be sufficient to coagulate the blood in the vessel 374 and collapse the vessel at that site.

In order to collapse a long length of the vessel 374, multiple treatment sites may be necessary. As shown in FIG. 18B, it is desirable to locate the first treatment site 380 at a downstream point with respect to the flow of blood in the vessel. The surgeon may then sequentially treat the vessel at multiple sites (382, 384, 386) upstream from the first site 380.

Figure 19:
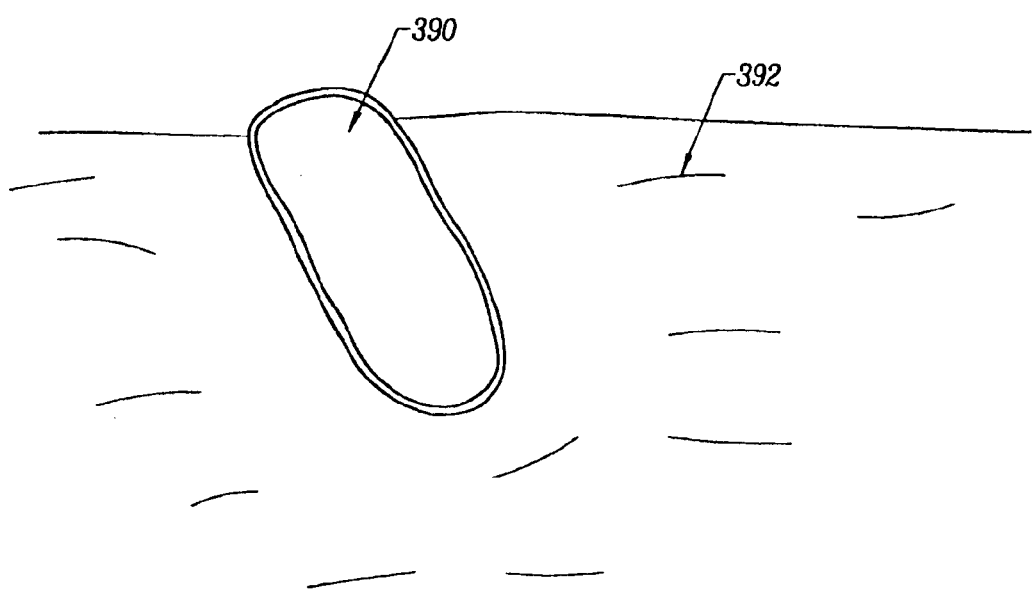
FIG. 19 illustrates a method of removing scalp tissue and/or hair according to the present invention.

Referring now to FIG. 19, a method for transplanting hair according to the present invention is described. A strip of hair (not shown) from a donor region is first excised from the patient. The hair may be excised by removing the tissue around the strip in a similar manner as described above. The hemostatic effects of the electrosurgical system of the present invention result in minimal bleeding at the donor site. The strip is then lifted from the scalp and sutures are used to close the opening.

Figure 20:
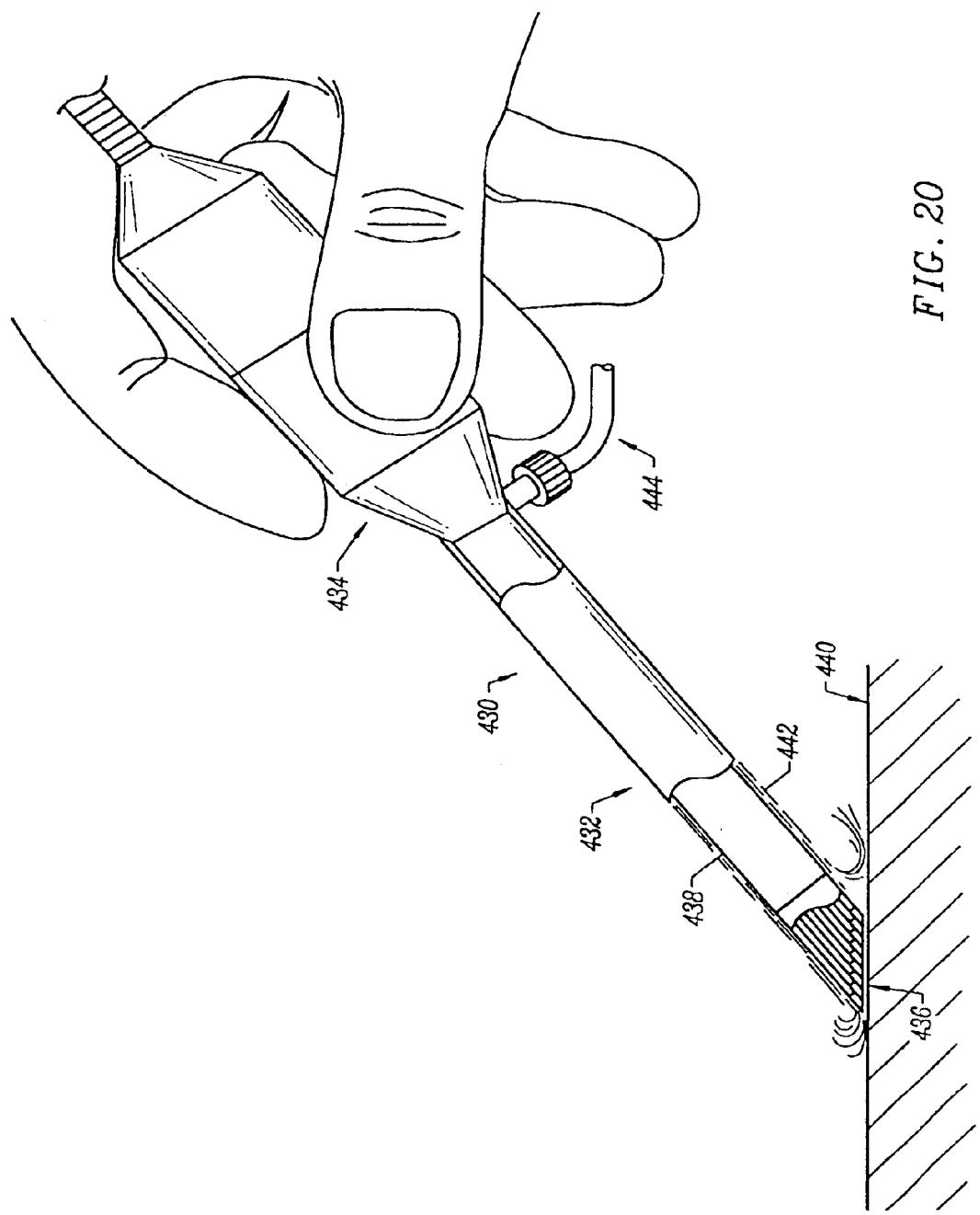
FIG. 20 is a cross-sectional view of an alternative electrosurgical probe for applying high frequency voltage to tissue layers on the skin.

One of the probes described above are then used to produce incisions 390 in the recipient area 392. As shown in FIG. 19, the depth an diameter of the incision 390 can be accurately controlled. The incisions are preferably formed at an angle to improve the retention of the graft and to form a more cosmetically suitable appearance. FIG. 20 illustrates an alternative embodiment, where an electrosurgical probe 430 is utilized to remove the surface layers of the epidermis 440. Probe 430 includes a shaft 432 coupled to a proximal handle 434 for holding and controlling shaft 432. Similar to previous embodiments, probe 430 includes an active electrode array 436 at the distal tip of shaft 432, an annular return electrode 438 extending through shaft 432 and proximally recessed from the, active electrode array 436 and an annular lumen 442 between return electrode 438 and an outer insulating sheath 444. Probe 430 further includes a liquid supply conduit 446 attached to handle 434 and in fluid communication with lumen 442 and a source of electrically conducting fluid (not shown) for delivering the fluid past return electrode 438 to the target site on the epidermis 440. As discussed above, electrode array 436 is preferably flush with the distal end of shaft 432 or distally extended from the distal end by a small distance (on the order of 0.005 inches) so to minimize the depth of ablation. Preferably, the distal end of shaft 432 is beveled to improve access and control of probe 430 while treating the epidermal tissue.

Figure 22:
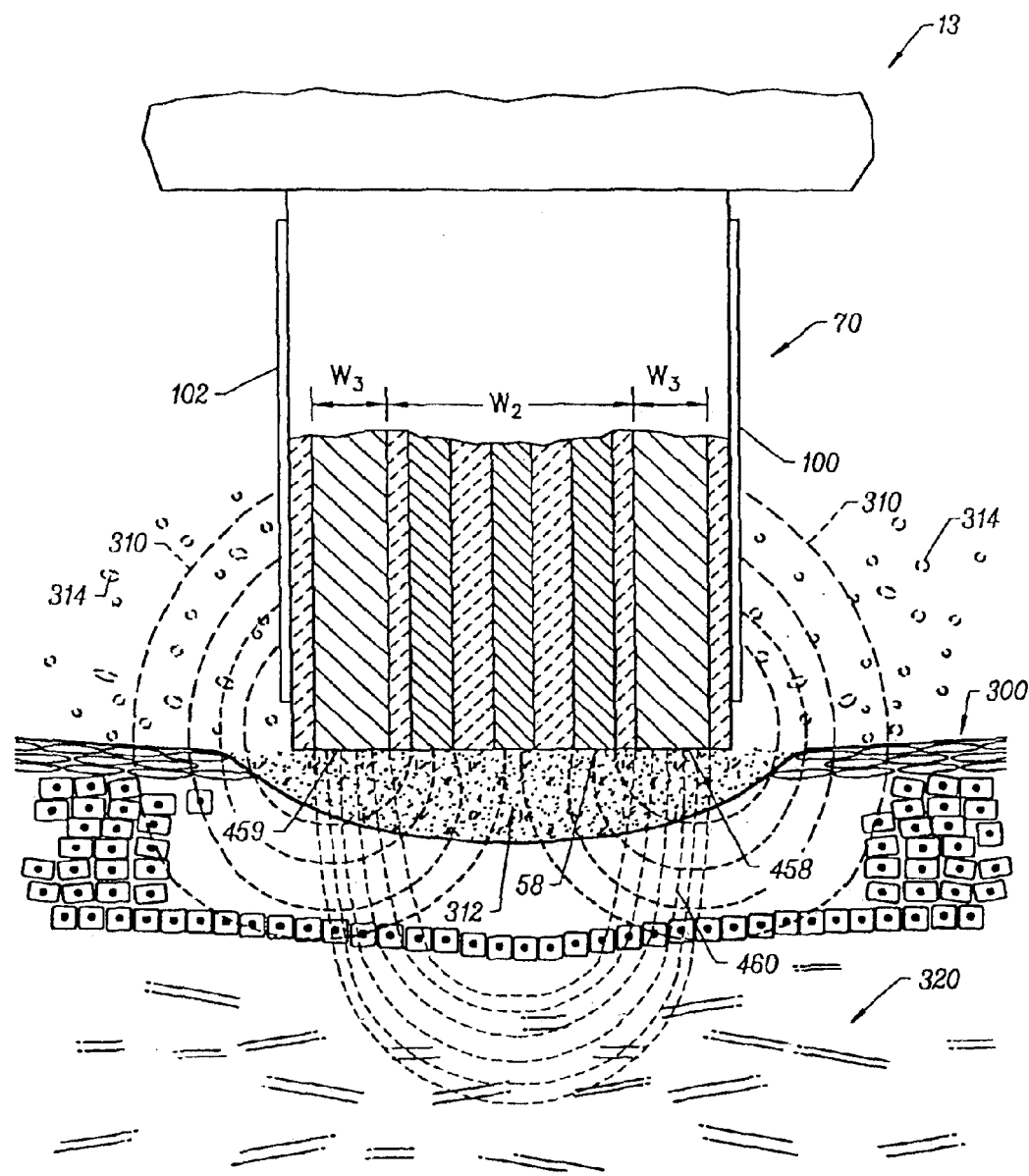
FIG. 22 illustrates another embodiment of the probe of the present invention, incorporating additional electrodes sized for contraction of tissue.

Yet another embodiment of the present invention is shown in FIG. 22. This embodiment is similar to that shown in FIG. 16 and described above with the exception that additional electrode terminals 458, 459 are positioned at the distal tip 70 of the probe. Electrode terminals 458, 459 may be the same size as ablation electrode terminals 58, larger as shown in FIG. 22. One operating arrangement is to connect electrode terminals 458, 459 to two poles of a high frequency generator to form a bipolar circuit allowing current to flow between terminals 458, 459 as shown by current flux lines 460. The electrode terminals 458, 459 are electrically isolated from ablation electrodes 58. By proper selection of the interelectrode spacing, $W_2$, and electrode width, $W_3$, and the frequency, the current flux lines 460 can be caused to flow below the epidermis layer to effect collagen shrinkage in region 320 as described hereinabove.

The voltage will preferably be sufficient to establish high electric field intensities between the active electrode array 436 and the epidermal tissue 440 to thereby induce molecular breakdown or disintegration of several cell layers of the epidermal tissue. As described above, a sufficient voltage will be applied to develop a thin layer of vapor within the electrically conducting fluid and to ionize the vaporized layer or region between the active electrode(s) and the target tissue. Energy in the form of photons and/or energetic electrons are discharged from the vapor layer to ablate the epidermal tissue, thereby minimizing necrosis of surrounding tissue and underlying cell layers, such as cell structures in the stratum lucidium and/or stratum granulosum.

Figure 23:
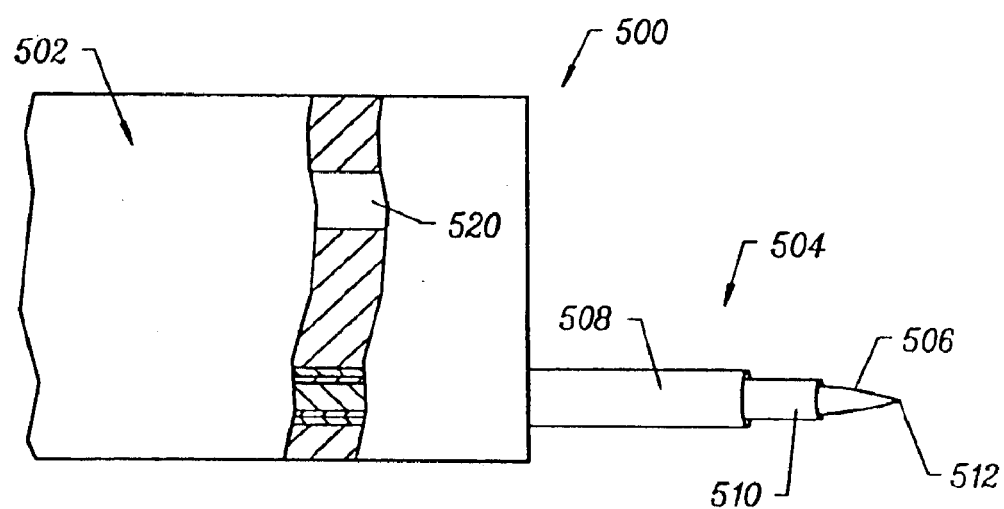
FIG. 23 illustrates another embodiment of the probe of the present invention, specifically designed for creating incisions in external skin surfaces.

FIG. 23 illustrates a distal portion of another electrosurgical probe 500 according to the present invention, particularly useful for cutting or creating incisions in an external skin surface. Probe 500 comprises a support member 502 coupled to a shaft or disposable tip (not shown) as described in previous embodiments. Support member 502 preferably comprises an inorganic electrically insulating material, such as ceramic, glass or glass-ceramic. In this embodiment, however, support member 502 may comprise an organic material, such as plastic, because the active electrode 506 and return electrode 508 are both spaced away from support member 502. Thus, the high intensity electric fields may be far enough away from support member 502 so as to allow an organic material.

An electrode assembly 504 extends from a distal end of support member 502, preferably a distance of about 2 to 20 mm. Electrode assembly 504 comprises a single, active electrode 506 and a return electrode sleeve 508 spaced proximally from active electrode 506 by an insulation member 510, which preferably comprises an inorganic material, such as ceramic, glass or glass-ceramic. As shown, active electrode 506 preferably tapers to a sharp distal end 512 to facilitate the cutting or incising of tissue.

In the exemplary embodiment, active electrode 506 has a proximal diameter of about 0.2 to 20 mm and a distal diameter of less than about 0.2 mm. Return electrode 508 is spaced from active electrode 506 a sufficient distance to prevent shorting or arcing therebetween at sufficient voltages to allow the volumetric removal of tissue. In the representative embodiment, the distal exposed portion of return electrode 508 is spaced about 0.5 to about 5 mm from the proximal exposed portion of active electrode 506. Of course, it will be recognized that the present invention is not limited to the particular dimensions and configuration of the electrode assembly 504 described herein, and a variety of different embodiments may be envisioned depending on the surgical application.

As shown, probe 500 includes a fluid lumen 520 passing through support member 502 to a distal opening (not shown) at the distal end of support member 502. Fluid lumen 520 is coupled to a supply of electrically conductive fluid, such as isotonic saline, or other suitable conductive fluid for delivery of such fluid to the target site. In the exemplary embodiment, the probe is designed such that lumen 520 will be positioned above electrode assembly 504 during use such that the conductive fluid exiting the distal opening of lumen 520 will naturally pass over return electrode 508 and active electrode 506 thereby creating a current path therebetween. In addition, the conductive fluid will sufficient cover the active electrode 506 such that the conditions for plasma formation can be met, as described in detail above.

Figure 24:
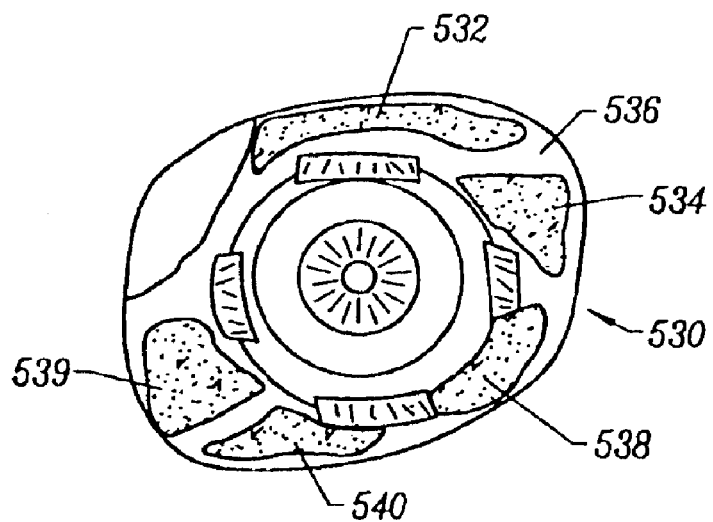
FIGS. 24–26 illustrates a method according to the present invention for removing fatty tissue under the eyelids to treat "baggy eyelids" syndrome.
Figure 25:
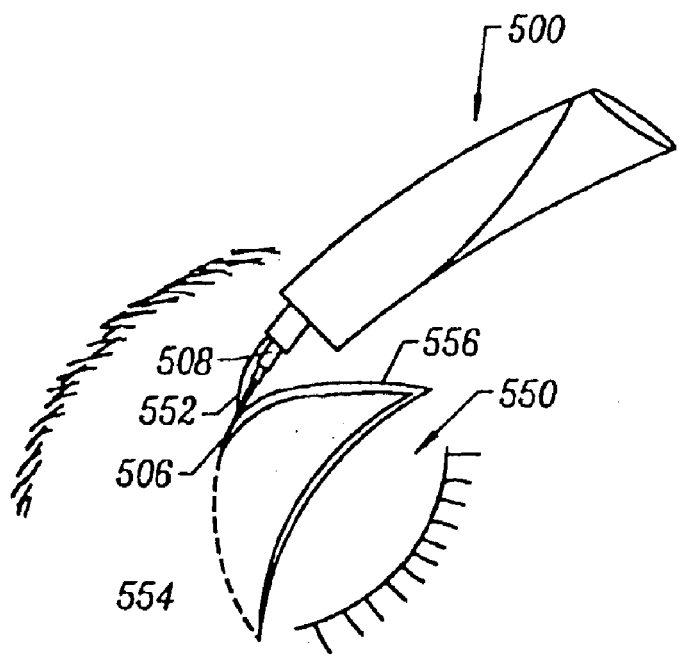
Figure 26:
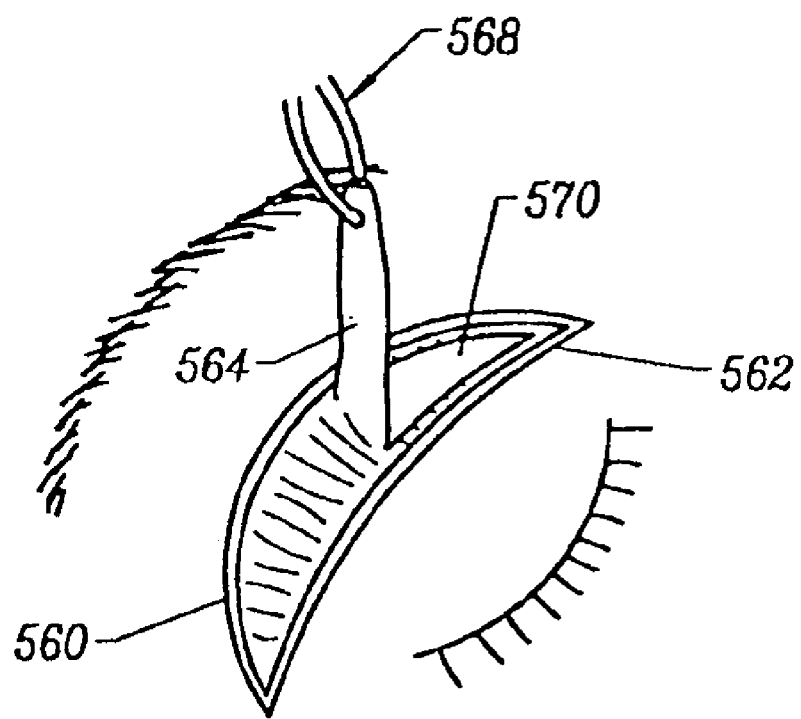

Referring now to FIGS. 24–26, a blepharoplasty procedure for removing fatty tissue underlying a patient's eyelids will now be described according to the present invention. As shown in FIG. 24, a front view of the orbit of the eye 530 reveals the important periocular structures relevant to blepharoplasty surgery. As shown, the two fat compartments of the upper lid, the central and medial compartments 532, 534, are divided by the superior oblique muscle 536. The inferior orbital fat is divided into three compartments, the medial compartment 538, the lateral fat compartment 539 and the central fat compartment 540. Medial fat has more blood vessels and nerves than the other fat compartments in both the upper and lower eyelid. Accordingly, this fat is more sensitive to the application of energy in conventional systems. Depending on the particular procedure, the present invention is designed to facilitate access to these fat compartments of the upper and lower eyelids such that a portion of the fat therein can be removed to treat "baggy eyelids" syndrome.

As shown in FIG. 25, the electrosurgical probe 500 is positioned adjacent the target area, in this case the patient's upper eyelid 550. The power supply is activated such that a high frequency voltage difference is applied between the active and return electrodes 506, 508 and electrically conductive fluid 552 is delivered to the target area, either by gravity, pump or other means. The surgeon then positioned that tip of the active electrode 506 adjacent to or in contact with the external skin 554, and translates the tip across the upper eyelid 550 to form an incision 556 therein. As discussed previously, the high frequency voltage is sufficient to convert the electrically conductive fluid between the target tissue and active electrode 506 into an ionized vapor layer or plasma. As a result of the applied voltage difference between active electrode 506 and the target tissue (i.e., the voltage gradient across the plasma layer), charged particles in the plasma (viz., electrons) are accelerated towards the tissue. At sufficiently high voltage differences, these charged particles gain sufficient energy to cause dissociation of the molecular bonds within tissue structures. This molecular dissociation is accompanied by the volumetric removal (i.e., ablative sublimation) of tissue and the production of low molecular weight gases, such as oxygen, nitrogen, carbon dioxide, hydrogen and methane. The short range of the accelerated charged particles within the target tissue confines the molecular dissociation process to the surface layer to minimize damage and necrosis to the underlying tissue.

As shown in FIG. 26, the surgeon will typically create an upper incision line 560 and a lower incision line 562 to form a crescent shaped flap of skin 564 between the two incision lines 560, 562. The flap of skin 564 is then removed, either completely or by folding it over with a pair of forceps 568, to expose the underlying orbital septum 570. The orbital septum 570 is then pierced with the electrosurgical probe of the present invention or with conventional tools, such as a scalpel, and the underlying fat is excised, e.g., with forceps or other conventional tools. During excision of fat, the probe 500 may be used to effect hemostasis of any severed blood vessels within the fat tissue. Once the desired amount of fat tissue has been removed, the surgeon reattaches the flap of skin 564 and cleans ups the surgical site.

Other modifications and variations can be made to disclose embodiments without departing from the subject invention as defined in the following claims. For example, FIG. 27 illustrates yet another embodiment designed for cutting of body structures, particularly creating incisions in external skin surfaces. In this embodiment, the electrode terminals 604 are arranged in a linear or columnar array of one of more closely spaced columns so that as the electrodes 604 are moved along the longer axis (denoted by arrow 660 in FIG. 27), the current flux lines are narrowly confined at the tip of the electrode terminals 604 and result in a cutting effect in the body structure being treated. As before, the current flux lines 660 emanating from the electrode terminals 604 pass through the electrically conducting liquid to the return electrode structure 612 located proximal to the probe tip.

Referring now to FIGS. 28 and 29, alternative geometries are shown for the electrode terminals 604. These alternative electrode geometries allow the electrical current densities emanating from the electrode terminals 604 to be concentrated to achieve an increased ablation rate and/or a more concentrated ablation effect due to the fact that sharper edges (i.e., regions of smaller radii of curvature) result in higher current densities. FIG. 28 illustrates a flattened extension of a round wire electrode terminal 604 which results in higher current densities at the edges 680. Another example is shown in FIG. 29 in which the electrode terminal 604 is formed into a cone shaped point 682 resulting in higher current densities at the tip of the cone.

Figure 30:
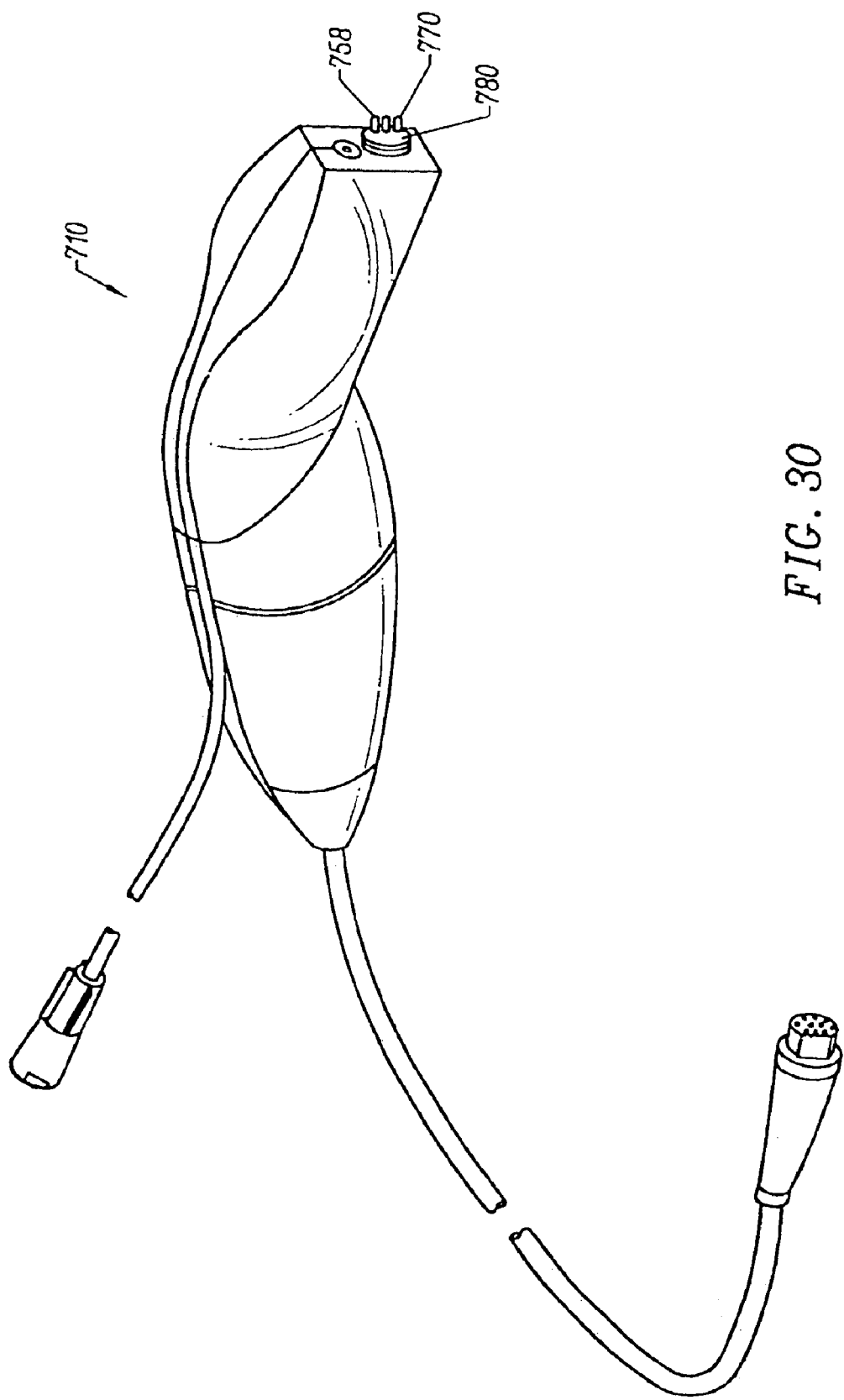
FIG. 30 is a perspective view of another embodiment of an electrosurgical probe for use in dermatology procedures.

FIG. 30 illustrates yet another embodiment of a probe 710 designed for cutting or incising tissue. As shown, in the embodiment, the electrically isolated electrode terminals 758 are spaced apart over a tissue treatment surface 780 of the electrode support member 770, preferably in a linear array. In the representative embodiment, three electrode terminals 758, each having a substantially conical shape, are arranged in a linear array extending distally from surface 780. Electrode terminals 758 will usually extend a distance of about 0.5 to 20 mm from tissue treatment surface 780, preferably about 1 to 5 mm. Applicant has found that this configuration increases the electric field intensities and associated current densities at the distal edges of electrode terminals 758, which increases the rate of tissue cutting. In the representative embodiment, the tissue treatment surface 780 has a circular cross-sectional shape with a diameter in the range of about 0.5 mm to 20 mm (preferably about 2 to 10 mm). The individual electrode terminals 758 preferably taper outward as shown, or they may form a distal edge, such as the electrodes shown in FIG. 28.

Figure 31:
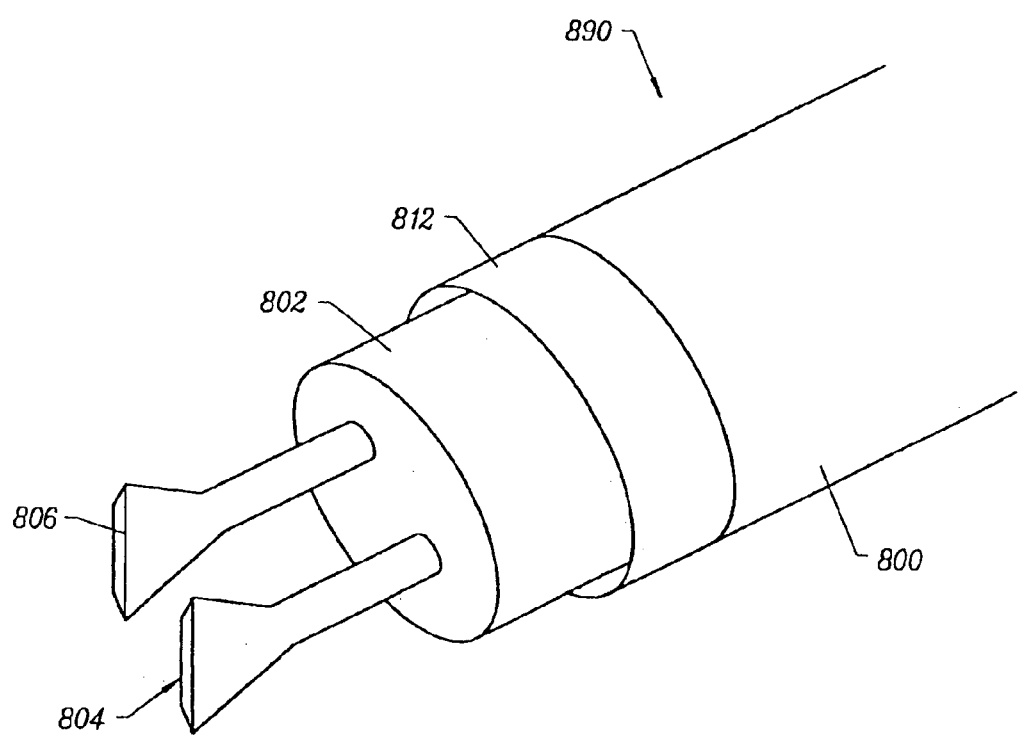
FIG. 31 is a detailed view of the distal portion of yet another electrosurgical probe according to the present invention.

FIG. 31 illustrates an electrosurgical probe 890 comprising a shaft 800 and at least two electrode terminals 804 extending from a support matrix 802 at the distal end of the shaft. The electrode terminals 804 preferably define a distal edge 806 for cutting an incision in tissue. The edges 806 of the electrode terminals 804 are substantially parallel with each other and usually spaced a distance of about 4 to 15 mm, preferably about 8–10 mm. The edges 806 extend from the distal end of support matrix 802 by a distance of about 0.5 to 10 mm, preferably about 2 to 5 mm. In the exemplary embodiment, probe 890 will include a return electrode 812 spaced proximally from the electrode terminals 804. Alternatively, the return electrode 812 may be one of the electrode terminals 804, or it may be a dispersive pad located on an external surface of the patient's body.

What is claimed is:

1. A method for removing tissue from a patient comprising:
   positioning an electrode terminal and a return electrode in close proximity to tissue at a target site on the patient;
   applying a high frequency voltage difference between the electrode terminal and the return electrode; and
   during the applying step, translating the electrode terminal across the external body surface to create an incision in the tissue without contacting the return electrode to the tissue.

2. The method of claim 1 wherein the tissue comprises a tissue structure in the papillary dermis or the epidermis.

3. The method of claim 1 further comprising removing a layer of an external body surface from the target site and removing a portion of the underlying fatty tissue.

4. The method of claim 1 further comprising effecting tissue hemostasis during the translating step.

5. The method of claim 1 further comprising delivering electrically conducting fluid to the target site, and contacting the electrically conducting fluid with the return electrode to provide a current flow path from the electrode terminal, through the electrically conducting fluid, and to the return electrode.

6. The method of claim 1 further comprising locating an electrically conducting gel on the tissue to provide a current flow path from the electrode terminal, through the electrically conducting fluid, and to the return electrode.

7. The method of claim 1 further comprising positioning the return electrode proximal to the electrode terminal to induce current flow from the electrode terminal away from the target site.

8. The method of claim 1 further comprising directing electrically conducting fluid along a fluid path past the electrode terminal and the return electrode to generate a current flow path between the return electrode and the electrode terminal.

9. The method of claim 1 wherein the electrode terminal comprises a single, elongate electrode terminal having a sharp distal tip.

10. The method of claim 1 wherein further comprising applying a sufficient high frequency voltage difference between the return electrode and the electrode terminal to remove the tissue through molecular dissociation or disintegration.

11. The method of claim 1 further comprising applying sufficient voltage to the electrode terminal in the presence of an electrically conductive fluid to vaporize at least a portion of the fluid between the electrode terminal and the tissue.

12. The method of claim 11, wherein the tissue comprises a tissue structure in the papillary dermis or the epidermis, the method further comprising accelerating charged particles from the vaporized fluid to a portion of the tissue structure to cause dissociation of the molecular bonds within the tissue structure.

\* \* \* \* \*